United States Patent
Puzio et al.

(12)

(10) Patent No.: US 6,448,471 B1
(45) Date of Patent: Sep. 10, 2002

(54) NEMATODE-FEEDING STRUCTURE SPECIFIC GENE AND ITS APPLICATION TO PRODUCE NEMATODE RESISTANT PLANTS

(76) Inventors: Piotr S. Puzio, Institut Fur Phytopathologie, University of Kiel, D-24098 Kiel (DE); Florian M. W. Grundler, Institut Fur Phytopathologie, University of Kiel, D-24098 Kiel (DE)

( * ) Notice: Subject to any disclaimer, the term of this patent is extended or adjusted under 35 U.S.C. 154(b) by 0 days.

(21) Appl. No.: 09/234,827

(22) Filed: Jan. 21, 1999

Related U.S. Application Data

(60) Provisional application No. 60/072,142, filed on Jan. 22, 1998.

(51) Int. Cl.⁷ .......................... A01H 3/00; C07H 21/04; C12N 5/14; C12N 15/09
(52) U.S. Cl. ...................... 800/278; 800/279; 800/287; 800/290; 800/298; 800/301; 800/306; 536/23.1; 536/24.1; 435/69.1; 435/410; 435/418; 435/419; 435/243; 435/252.3
(58) Field of Search .................................. 800/278, 279, 800/287, 290, 298, 301, 306; 536/23.1, 24.1; 435/69.1, 468, 410, 418, 419, 243, 320.1, 252.3

(56) References Cited

FOREIGN PATENT DOCUMENTS

| WO | WO 93/0251 | * 5/1993 |
| WO | WO9746692 | * 12/1997 |

OTHER PUBLICATIONS

Barthels et al. The Plant Cell. 1997. Dec. issue. vol. 9: 2119–2134.*

Kim et al. Plant Molecular Biology. 1994. vol. 24: 105–117.*

Chen et al. Plant J. 1996. Dec. issue. 10:6 955–966.*

* cited by examiner

*Primary Examiner*—Phuong T. Bui
(74) *Attorney, Agent, or Firm*—Ladas & Parry

(57) ABSTRACT

The invention provides a regulatory DNA sequence obtainable from Arabidopsis thaliana that is capable of promoting root knot and cyst nematode-inducible transcription of an associated DNA sequence when re-introduced into a plant, a gene sequence which is specifically expressed in the nematode feeding structure and the use of the regulatory DNA sequence.

19 Claims, 2 Drawing Sheets

US 6,448,471 B1

NEMATODE-FEEDING STRUCTURE SPECIFIC GENE AND ITS APPLICATION TO PRODUCE NEMATODE RESISTANT PLANTS

This application claims the benefit of U.S. Provisional Application No. 60/072,142 filed Jan. 22, 1998.

The invention relates to a gene which is specifically expressed in nematode feeding structures, the promoter which regulates said expression and methods for making plants that are resistant, or at least less susceptible to plant parasitic nematodes, or their effects, as well as to cells, plants and parts thereof.

STATE OF THE ART

In International patent application WO92/17054, a method is disclosed for the identification and subsequent isolation of nematode responsive regulatory DNA sequences from *Arabidopsis thaliana*.

In WO 92/21757 several nematode-inducible regulatory DNA sequences have been isolated from *Lycopersicon esculentum*, which are responsive to the root-knot nematode *Meloidogyne incognita*. Some of these regulatory sequences (LEMMI's, for *Lycopersicon eaculentum—Meloidogyne incognita*) are stimulated, whereas others appear to be repressed by the nematode. of one of the responsive sequences LEMMI-9, the gene which is expressed by said regulatory sequence was elucidated, which showed to be homologous to LEA, a seed storage protein.

Another regulatory sequence that is inducible by the root-knot nematode *Meloidogyne incognita* is disclosed in WO 93/06710. Also here the gene normally expressed by this TobRb7 regulatory sequence was elucidated and it appears to be coding for a water-pore which facilitates water transport from the xylem to the cell. Recently, it has been reported that antisense expression of this gene in tobacco (the plant in which it naturally occurs) gives a decrease in infectibility by nematodes (Opperman, C. H. and Conkling, M. H., Third Int. Nematol. Congr. Guadeloupe, 1996, S-62). A disadvantage of this regulatory sequence TobRb7 is that it is not activated by a number of cyst nematodes, among which the Heterodera and Globodera species. This makes the TobRB7 sequence unsuitable for use in chimerical constructs aiming at, for example, cyst nematode resistance in potato.

It is an object of the invention to provide a gene with its regulatory DNA sequences which is at least inducible by both cyst nematodes and which can be used to suppress the presence and/or the function of the naturally occurring protein inside the feeding structure of the nematode, thereby conferring resistance to nematodes.

SUMMARY OF THE INVENTION

The invention provides a polynucleotide obtainable from *Arabidopsis thaliana* that is encoding a protein and its regulatory sequence which is specifically expressed in nematode feeding structures. Preferably the protein is having an amino acid sequence according to SEQ ID NO:2, SEQ ID NO:4 or a mutein thereof. Preferably the nucleotide sequence according to the invention is the sequence represented in SEQ ID NO:1 or SEQ ID NO:3. Also part of the invention is the regulatory sequence capable of promoting root knot and cyst nematode-inducible transcription of an associated DNA sequence when re-introduced into a plant. Preferably this regulatory sequence is the sequence depicted from nucleotide 1 to 4037 in SEQ ID NO:1 or pieces thereof which still can direct specific expression. A still further preferred aspect of the invention comprises a regulatory DNA fragment that is substantially nematode feeding site-specific.

Further embodiments of the invention comprise chimerical DNA sequences comprising a DNA sequence coding for (part of) the nematode feeding site specific protein of the invention, but expressed in antisense order, in order to block endogenous mRNA coding for the endogenous protein and thus giving resistance to nematodes. The regulatory element can further be used in chimerical DNA sequences comprising in the direction of transcription a regulatory DNA fragment according to the invention and a DNA sequence to be expressed under the transcriptional control thereof and which is not naturally under transcriptional control of said DNA fragment. Preferred among the chimerical DNA sequences according to the invention are those wherein the DNA sequence to be expressed causes the production of a plant cell-disruptive substance, such as barnase. In a different embodiment the cell-disruptive substance comprises RNA complementary to RNA essential to cell viability. Yet in another embodiment the DNA sequence to be expressed causes the production of a substance toxic to the inducing nematode.

The invention finds further use in a replicon comprising a DNA fragment or chimerical DNA sequence according to the invention, a microorganism containing such a replicon, as well as plant cells having incorporated into their genome a chimerical DNA sequence according to the invention. Further useful embodiments are a root system of a plant essentially consisting of cells according to the invention, as well as full grown plants essentially consisting of cells according to the invention, preferably a dicotyledonous plant, more preferably a potato plant. Also envisaged are plants grafted on a root system according to the invention, as well as plant parts selected from seeds, flowers, tubers, roots, leaves, fruits, pollen and wood and crops comprising such plants.

The invention also encompasses the method of antisense expression of the protein of the invention, thereby blocking expression of the endogenous protein and thereby inhibiting the formation and/or further development of a nematode feeding structure which will give resistance to nematode infection.

The invention further provides the use of a fragment, portion or variant of a regulatory DNA according to the invention for making hybrid regulatory DNA sequences.

Figure 1:
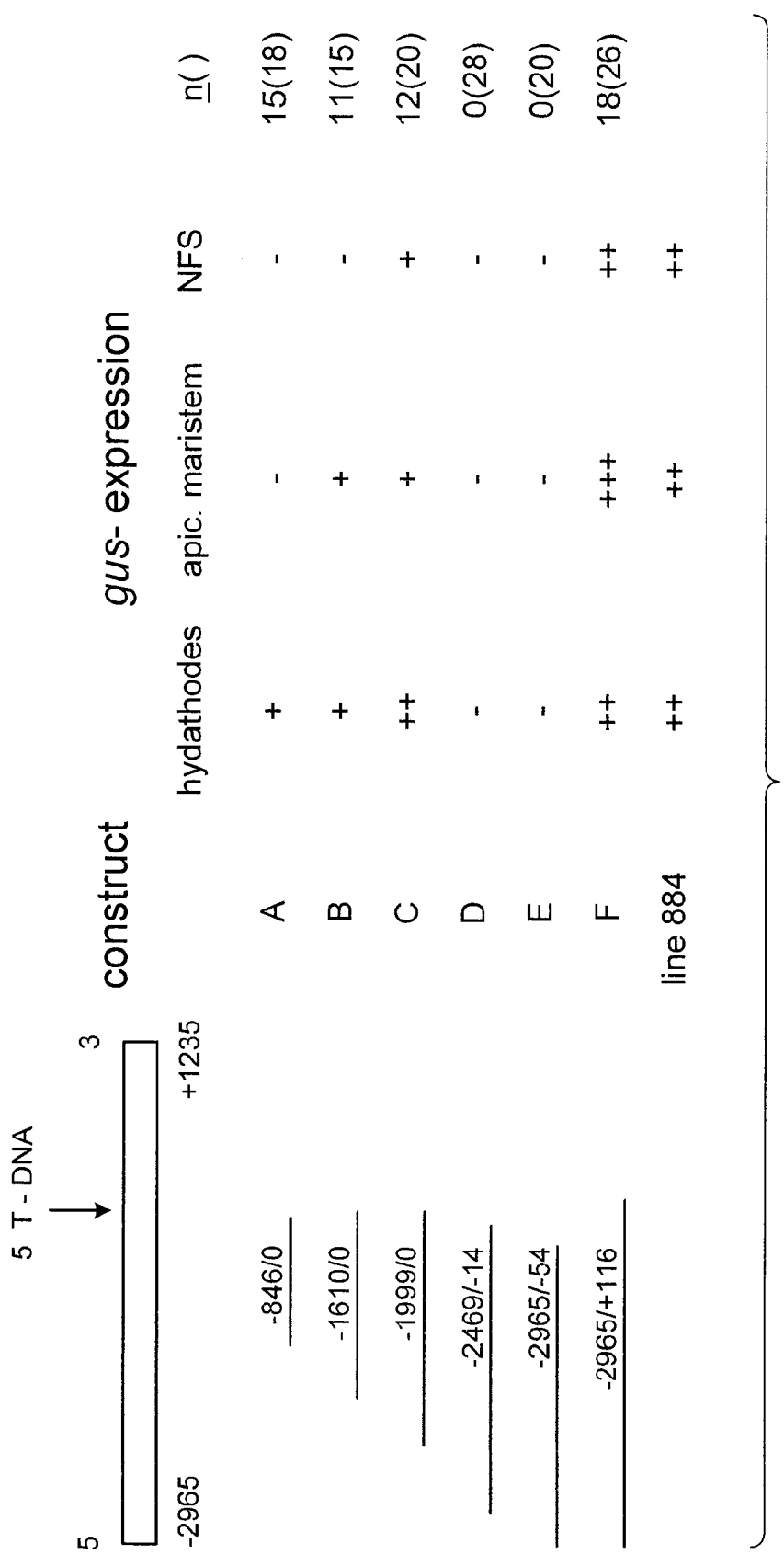
FIG. 1. The genomic organization of the T-DNA insertion site in *A. thaliana* line #884 and the construction of transformation vectors with promoter fragments with the results of the gus expression analysis. The T-DNA insertion site in line #884 is indicated with an arrowhead. Numbering of basepairs is relative to the putative start of transcription. The activity of gus in hydathodes, apical meristem in shoot and in the nematode feeding structures (NFS), as visually determined, is indicated. n is the number of gus expressing transformant lines, the number of tested plants per construct is indicated between brackets.

Some ways of practicing the invention as well as the meaning of various phrases are explained in more detail below.

DETAILED DESCRIPTION OF THE INVENTION

The protein according to the present invention may be obtained by isolating it from *Arabidopsis thaliana* or from any suitable plant source material containing it.

The word protein means a sequence of amino acids connected trough peptide bonds. Polypeptides or peptides are also considered to be proteins. Muteins of the protein of the invention are proteins that are obtained from the proteins depicted in the sequence listing by replacing, adding and/or deleting one or more amino acids, while still retaining their activity. Such muteins can readily be made by protein engineering in vivo, e.g. by changing the open reading frame capable of encoding the protein so that the amino acid sequence is thereby affected. As long as the changes in the amino acid sequences do not altogether abolish the activity of the protein such muteins are embraced in the present invention. Further, it should be understood that muteins should be derivable from the proteins depicted in the sequence listing while retaining biological activity, i.e. all, or a great part of the intermediates between the mutein and the protein depicted in the sequence listing should have biological activity. A great part would mean 30% or more of the intermediates, preferably 40% of more, more preferably 50% or more, more preferably 60% or more, more preferably 70% or more, more preferably 80% or more, more preferably 90% or more, more preferably 95% or more, more preferably 99% or more.

Subsequently, polynucleotides encoding said proteins according to the invention may be obtained by elucidating the amino acid sequence of said promoter, by developing a number of primers coding specifically for conserved parts of said protein and using these primers to pick up related sequences from DNA libraries.

The present invention provides a chimerical DNA sequence which comprises an open reading frame capable of encoding a protein according to the invention. The expression chimerical DNA sequence shall mean to comprise any DNA sequence which comprises DNA sequences not naturally found in nature. For instance, chimerical DNA shall mean to comprise DNA comprising the said open reading frame in a non-natural location of the plant genome, notwithstanding the fact that said plant genome normally contains a copy of the said open reading frame in its natural chromosomal location. Similarly, the said open reading frame may be incorporated in the plant genome wherein it is not naturally found, or in a replicon or vector where it is not naturally found, such as a bacterial plasmid or a viral vector. Chimerical DNA shall not be limited to DNA molecules which are replicable in a host, but shall also mean to comprise DNA capable of being ligated into a replicon, for instance by virtue of specific adapter sequences, physically linked to the open reading frame according to the invention. The open reading frame may or may not be linked to its natural upstream and downstream regulatory elements.

The open reading frame may be derived from a genomic library. In this latter it may contain one or more introns separating the exons making up the open reading frame that encodes a protein according to the invention. The open reading frame may also be encoded by one uninterrupted exon, or by a cDNA complementary to the mRNA encoding a protein according to the invention. Open reading frames according to the invention also comprise those in which one or more introns have been artificially removed or added. Each of these variants is embraced by the present invention.

In order to be capable of being expressed in a host cell a chimerical DNA according to the invention will usually be provided with regulatory elements enabling it to be recognized by the biochemical machinery of the host and allowing for the open reading frame to be transcribed and/or translated in the host. It will usually comprise a transcriptional initiation region which may be suitably derived from any gene capable of being expressed in the host cell of choice, as well as a translational initiation region for ribosome recognition and attachment. In eukaryotic cells, an expression cassette usually comprises in addition a transcriptional termination region located downstream of said open reading frame, allowing transcription to terminate and polyadenylation of the primary transcript to occur. In addition, the codon usage may be adapted to accepted codon usage of the host of choice. The principles governing the expression of a chimerical DNA construct in a chosen host cell are commonly understood by those of ordinary skill in the art and the construction of expressible chimerical DNA constructs is now routine for any sort of host cell, be it prokaryotic or eukaryotic.

In order for the open reading frame to be maintained in a host cell it will usually be provided in the form of a replicon comprising said open reading frame according to the invention linked to DNA which is recognized and replicated by the chosen host cell. Accordingly the selection of the replicon is determined largely by the host cell of choice. Such principles as govern the selection of suitable replicons for a particular chosen host are well within the realm of the ordinary skilled person in the art.

A special type of replicon is one capable of transferring itself, or a part thereof, to another host cell, such as a plant cell, thereby co-transferring the open reading frame according to the invention to said plant cell. Replicons with such capability are herein referred to as vectors. An example of such vector is a Ti-plasmid vector which, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer chimerical DNA sequences into plant cells, or protoplasts, from which new plants may be generated which stably incorporate said chimerical DNA in their genomes. A particularly preferred form of Ti-plasmid vectors are the so-called binary vectors as claimed in (EP 0 120 516 B1 and U.S. Pat. No. 4,940, 838). other suitable vectors, which may be used to introduce DNA according to the invention into a plant host, may be selected from the viral vectors, e.g. non-integrative plant viral vectors, such as derivable from the double stranded plant viruses (e.g. CaMV) and single stranded viruses, gemini viruses and the like. The use of such vectors may be advantageous, particularly when it is difficult to stably transform the plant host. Such may be the case with woody species, especially trees and vines.

The expression "host cells incorporating a chimerical DNA sequence according to the invention in their genome" shall mean to comprise cells, as well as multicellular organisms comprising such cells, or essentially consisting of such cells, which stably incorporate said chimerical DNA into their genome thereby maintaining the chimerical DNA, and preferably transmitting a copy of such chimerical DNA to progeny cells, be it through mitosis or meiosis. According to a preferred embodiment of the invention plants are provided, which essentially consist of cells which incorporate one or more copies of said chimerical DNA into their genome, and which are capable of transmitting a copy or copies to their progeny, preferably in a Mendelian fashion. By virtue of the transcription and translation of the chimerical DNA according to the invention in some or all of the plant's cells, those cells as produce the protein(s) according to the invention will show enhanced resistance to nematode infections. Although the principles as govern transcription of DNA in plant cells are not always understood, the creation of chimerical DNA capable of being expressed in substantially a constitutive fashion, that is, in substantially most cell types of the plant and substantially without serious temporal and/or developmental restrictions, is now routine.

Nematode resistance is achieved mainly by prohibiting the development of a nematode feeding site by damaging or disrupting it. This can be done by toxins, but also by prohibiting expression of essential endogenous genes. One way of doing this is by transformation of a plant with a gene construct comprising an inhibitory gene which may comprise a sense gene which is essentially identical to the target-gene, which upon proper expression inhibits the target-gene according to a yet unknown mechanism referred to as sense-sense inhibition or co-suppression (International Patent Application WO 90/11682, DNA Plant Technology inc.). Recently a review on this gene silencing (as it is alternatively called) has appeared (Matzke, M. A. and Matzke, A. J. M., Plant Physiol. 107, 679–685, 1995) in which three possible explanations of silencing have been described.

Preferably the inhibitory gene is an antisense gene directed against the target-gene. The antisense gene does not necessarily need to be entirely complementary to the target gene, as long as its length and homology is enough to provide for a suitably high inhibition. Thus, the antisense gene may be (partially) complementary to the 5'-end of the of the corresponding target gene, the 3'-end, or the middle part, or (partially) complementary to the entire corresponding target gene. With partially complementary is meant the situation wherein the antisense gene is not fully complementary to the corresponding target gene, which may be due to the fact that e.g. the antisense gene is complementary to a heterologous gene(i.e. obtained from a different source). The antisense gene may be entirely synthetic as well. All these variations with respect to the choice of the antisense gene are not critical to the invention as long as the level of antisense homology, and/or the total amount of complementarity is sufficient to inhibit expression of the target gene.

The present invention further provides regulatory DNA sequences obtainable from *Arabidopsis thaliana*, which show a high preference of expression inside the special nematode feeding structures of the plant root.

In principle the regulatory DNA sequences according to the invention can be used to express any heterologous DNA in any plant of choice, by placing said DNA under the control of said regulatory DNA sequences and transforming plants with the resulting chimerical DNA sequence using known methods. The heterologous DNA is expressed upon infection of the roots by various root knot nematodes, such as *Meloidogyne incognita*, and cyst nematodes, such as *Heterodera schachtii* and *Clobodera pallida* (a more comprehensive, but by no means limiting, list is presented in table 1). Preferably, the heterologous DNA is a DNA sequence antisense to the DNA sequence coding for the protein of the invention. Alternatively, the heterologous DNA may consist of a gene coding for a substance that is toxic or inhibitive to a plant parasitic nematode in order to create plants with reduced susceptibility to plant parasitic nematodes. There exist numerous examples of such toxic substances, such as the endotoxins of *Bacillus thuringiensis* (e.g. EP 0 352 052), lectins, and the like.

A more preferred approach for making plants with reduced susceptibility to plant parasitic nematodes consists in the disruption of the specialized feeding structure of the plant roots by expressing a phytotoxic substance under the control of the regulatory DNA sequences according to the invention. The general principles of this approach have been disclosed and claimed in International patent applications WO 92/21757, WO 93/10251 and WO 94/10320, which are hereby incorporated by reference. For the sake of consistency, the phytotoxic substance shall be referred to hereinafter as the nematode feeding site (NFS) disruptive substance.

Although the regulatory DNA sequences according to the invention are relatively specific for the nematode feeding structure, it is envisaged that expression of NFS disruptive substances under the control thereof has adverse effects on plant viability and/or yield, due to expression in non-target (i.e. non-NFS) tissues, like hydathodes and apical meristems. In order to reduce or eliminate (potential) adverse effects, it is therefore strongly preferred to use a chimerical NFS-disruptive construct according to the invention in conjunction with a neutralizing gene construct. The details of such a so-called two-component approach for the engineering of nematode resistant plants are set out in WO 93/10251. According to this approach a NFS-disrupter gene (gene-A) is placed under the control of a promoter that is at least active in the NFS, and preferably not or hardly outside the NPS, whereas the unwanted phytotoxic effects outside the NFS are neutralized by a neutralizing gene (gene-B) that is expressed at least in those tissues wherein the disruptive substance is produced except for the NFS.

According to the two-component approach a suitable promoter-A is defined as a promoter that drives expression of a downstream gene coding for a disruptive substance inside the NFS, at levels sufficient to be detrimental to the metabolism and/or functioning and/or viability of the NFS, while this promoter should preferably, but not necessarily, be inactive in tissues outside the NPS; it should at least never be active outside NFS at such levels that the activity of the disruptive substance, encoded by gene-A, can not be neutralized sufficiently by products from gene-B.

The properties of the regulatory DNA sequences according to the invention, especially as indicated in Example 8, make them highly useful in the two-component approach. Obviously, numerous mutations are possible in the regulatory DNA sequences according to the invention which do not alter the properties of these sequences in a way crucial to their intended use. Such mutations do, therefore, not depart from the present invention.

Within the context of this invention, the terms NFS disruptive substance and neutralizing substance embraces a series of selected compounds that are encoded by DNA whose gene products (either protein or RNA or antisense-RNA) are detrimental to the metabolism and/or functioning and/or viability of NFS or organelles therein and for which neutralizing substances are known that are able, when expressed simultaneously in the same cell as the disruptive substance, to repress the activity of the disrupting substance. Preferred combinations of disrupting and neutralizing substances are e.g. barnase/barstar from *Bacillus amyloliquefaciens* (Hartley, 1988, J. Mol. Biol. 202, 913–915), restriction endonucleases/corresponding methylases such as EcoRI from *E. coli* (Green et al., 1981, J. Biol. Chem. 256, 2143–2153) and EcoRI methylase or similar combinations as described in the review for type II restriction modification systems (Wilson, 1991, Nucl. Acid Res. 19, 2539–2566), bacteriocins and corresponding immunity proteins, e.g. colicin E3/immunity protein from *E. coli* (Lau et al. 1985, Nucl. Acid Res. 12, 8733–8745) or any disruptive substance coding gene which may be neutralized by simultaneous production of antisense RNA under control of promoter-B, such as DNA sequences encoding Diptheria Toxin Chain A (Czako & An, 1991, Plant Physiol. 95, 687–692), RNAses such as RNAse T1, ribonucleases or proteases. A further possibility is to have a gene coding for a ribozyme active against mRNA that code for phytotoxic protein in the non target tissue (i.e. all tissues except the NFS).

According to another aspect of the invention combinations of disrupting and neutralizing substances comprise respectively genes inhibitory to an endogenous gene that encodes a protein or polypeptide product that is essential for cell viability and, as a neutralizing gene, a gene that encodes a protein or polypeptide product capable of substituting the function of the endogenous protein or polypeptide product.

According to the preferred embodiment of the invention use is made of the antisense gene corresponding to the protein of the invention to inhibit expression of the endogenous gene, which gene is expressed in the nematode feeding structures.

The disruptive effect brought about by the antisense gene inhibitory to the vital endogenous gene is neutralized by the expression of a neutralizing gene-B under the control of a promoter-B as defined, said gene-B when expressed produces a protein according to the invention. It is preferred that the nucleotide sequence of the RNA transcript encoded by the neutralizing gene is divergent from the endogenous gene RNA transcript to avoid a possible co-suppressive effect. As a rule the neutralization gene must not give rise to a transcript that is identical to the endogenous gene transcript. Preferably, the neutralization gene transcribed region is as much divergent from the transcribed region of the endogenous gene as possible, while the protein product encoded by said transcript is identical, or almost identical. It is well known in the art that each amino acid can be encoded by a more than one codon; this fact, referred to as the degeneracy of the genetic code, stems from the fact that there are about 20 different amino acids, which are encoded by triplets of four different bases, yielding a total of 64 possible codons. Three codons comprise stop signals for translation, so that actually 61 codons specify about 20 amino acids. Roughly spoken, every third base may be changed in a coding region without affecting the amino acid sequence of the protein. This means that the transcribed region of a neutralization gene can at least diverge 33% from the endogenous gene. But, since a gene transcript generally comprises non-translated regions flanking the coding region on both sides, even further nucleic acid divergence may be achieved in order to avoid interaction of the neutralization gene transcript with the endogenous gene transcript.

Furthermore, still greater divergence may be achieved if one takes into account the fact that two proteins may differ in their amino acid sequence, while retaining their physiological activity in the plant cell. Although it is not established to what extent this may be, it may be assumed that proteins which have conservative amino acid replacements in 10% of their amino acids, will still be capable of performing their physiological role. Altogether, it will be clear to someone skilled in the art that a neutralization gene according to the present invention need not be more identical to its endogenous counterpart than about 40–50% on the nucleic acid level.

A suitable promoter-B is defined as a promoter that drives expression in substantially all cells wherein gene-A is expressed, with the proviso that it does not drive expression inside a nematode feeding structure, or not effectively. (With 'substantially all cells' is meant at least those cells that should be viable in order to get normal plant growth and or development required for commercial exploitation of such plants). As an illustration of plants in which the disruptive effect is not neutralized in exactly all cells of the host plant and which are nevertheless viable and suitable for commercial exploitation, those which express a disrupter gene according to this invention in stamen cells can be mentioned; this may yield male-sterile plants, which is even regarded as a commercially attractive trait in some crops. In the case when the regulatory sequences according to this invention are used as promoter-A, promoter-B should be specifically active in the hydathodes and the apical meristems. Suitable examples of the promoter-B type can be obtained from plants or plant viruses, or may be chemically synthesized. The regulatory sequences may also include enhancer sequences, such as found in the 35S promoter of CaMV (Kay et al., 1987, Science 236, 1299–1302), and mRNA stabilizing sequences such as the leader sequence of Alfalfa Mosaic Virus RNA4 (Brederode et al., 1980, Nucl. Acids Res. 8, 2213–2223) or any other sequences functioning in a like manner.

The suitability of other constitutive promoters such as the nopaline synthase promoter (Bevan, 1984, Nucl. Acids Res. 12, 8711–8721) or figwort mosaic virus promoter (HP-A 426 641) for use as promoter-B can be tested through fusion to marker genes such as GUS (Jefferson, 1987, Plant Mol. Biol. Reporter 5, 387–405), transfer of these constructs to plants and histochemical analysis of such transgenic plants after infection with plant-parasitic nematodes (PPN).

Another method to bring about nematode resistance is by disrupting the nematode feeding structure through a so-called one-component system. Within this invention the system is based upon disruption of the nematode feeding structure by inhibiting the endogenous gene expression of the protein depicted in SEQ ID NO:2 (or muteins thereof). In non-transgenic plants this protein is expressed in the NFS and partially in other tissues like hydathodes and apical meristems of shoots. Inhibition of the expression by co-suppression or anti-sense expression will only function if a promoter is available which does specifically express the inhibiting construct in the nematode feeding structure and not in the other tissues mentioned. Several promoters are available which give specific expression in the NFS and not in the hydathodes and/or apical meristems. Examples of these promoters are the #1164 promoter (WO 97/46692) and the #25.1 promoter (WO 98/22599).

Other regulatory sequences such as terminator sequences and polyadenylation signals include any such sequence functioning as such in plants, the choice of which is within the level of skill of the average skilled person in the art. An example of such sequences is the 3' flanking region of the nopaline synthase (nos) gene of *Agrobacterium tumefaciens* (Bevan, 1984, Nucl. Acids Res. 12, 8711–8721).

Further details of the two component approach can be found in WO 93/10251 (herein incorporated by reference).

The choice of the plant species is primarily determined by the amount of damage through PPN infections estimated to occur in agriculture and the amenability of the plant species to transformation. Plant genera which are damaged during agricultural practice by PPN and which can be made significantly less susceptible to PPN by ways of the present invention include but are not limited to the genera mentioned in Table 1.

Nematode species as defined in the context of the present invention include all plant-parasitic nematodes that modify host cells into specially adapted feeding structures which range from migratory ectoparasites (e.g. Xiphinema spp.) to the more evolved sedentary endoparasites (e.g. Heteroderidae, Meloidogynae or Rotylenchulinae). A list of parasitic nematodes is given in Table 1, but the invention is not limited to the species mentioned in this table. More detailed listings are presented in Zuckerman et al. (eds., in: Plant Parasitic Nematodes, Vol. I 1971, New York, pp. 139–162).

TABLE 1

EXAMPLES OF PLANT-PARASITIC NEMATODES AND THEIR PRINCIPAL HOST PLANTS

| Nematode Species | Principal Host Plants |
|---|---|
| Meloidogyne | |
| M. hapla | wide range |
| M. incognita | wide range |
| M. exigua | coffee, tea, Capsicum, Citrullus |
| M. indica | Citrus |
| M. javanica | wide range |
| M. africana | coffee |
| M. graminis | cereals, grasses |
| M. graminicola | rice |
| M. arenaria | wide range |
| Heterodera & Globodera | |
| H. mexicana | Lycopersicon esculentum, Solanum spp. |
| H. punctata | cereals, grasses |
| G. rostochiensis | Solanum tuberosum, Solanum spp, Lycopersicon esculentum |
| G. pallida | Solanum tuberosum |
| G. tabacum | Nicotiana tabacum, Nicotiana spp. |
| H. cajani | Cajanus cajan, Vigna sinensis |
| H. glycines | Glycine max, Glycine spp. |
| H. oryzae | Oryza sativa |
| H. schachtii | Beta spp, Brassica spp, |
| H. trifolii | Trifolium spp. |
| H. avenae | cereals, grasses |
| H. carotae | Daucus carota |
| H. cruciferae | Cruciferae |
| H. goettingiana | Pisum sativum, Vicia spp. |

Within the context of this invention, a plant is said to show reduced susceptibility to plant parasitic nematodes if a statistically significant decrease in the number of mature females developing at the surface of plant roots can be observed as compared to control plants. Susceptible/ resistance classification according to the number of maturing females is standard practice both for cyst- and root-knot nematodes (e.g. LaMondia, 1991, Plant Disease 75, 453–454; Omwega et al., 1990, Phytopathol. 80, 745–748).

A nematode feeding structure according to the present invention shall include an initial feeding cell, which shall mean the cell or a very limited number of cells destined to become a nematode feeding structure, upon induction of the invading nematode.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle any transformation method may be used to introduce chimerical DNA according to the invention into a suitable ancestor cell. Methods may suitably be selected from the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-integrative) viruses, in planta Agrobacterium tumefaciens mediated gene transfer by infiltration of adult plants or transformation of mature pollen or microspores (EP 0 301 316) and the like. A preferred method according to the invention comprises Agrobacterium-mediated DNA transfer. Especially preferred is the use of the so-called binary vector technology as disclosed in EP A 120 516 and U.S. Pat. No. 4,940,838).

Tomato transformation is preferably done essentially as described by Van Roekel et al. (Van Roekel, J. S. C., Damim, B., Melchers, L. S., Hoekema, A. (1993). Factors influencing transformation frequency of tomato (Lycopersicon esculentum). Plant Cell Reports, 12, 644–647). Potato transformation is preferably done essentially as described by Hoekema et al. (Hoekema, A., Huisman, M. J., Molendijk, L., van den Elzen, P. J. M., and Cornelissen, B. J. C. (1989). The genetic engineering of two commercial potato cultivars for resistance to potato virus X. Bio/Technology 7, 273–278).

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or (tissue) electroporation (Shimamoto, et al, 1989, Nature 338, 274–276). Transgenic maize plants have been obtained by introducing the Streptomyces hygroscopicus bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting embryogenic callus for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as rice and corn are also amenable to DNA transfer by Agrobacterium strains (vide WO 94/00977; EP 0 159 418 B1; Gould J, Michael D, Hasegawa O, Ulian E C, Peterson G, Smith R H, (1991) Plant. Physiol. 95, 426–434).

To obtain transgenic plants capable of constitutively expressing more than one chimerical gene, a number of alternatives are available including the following:

A. The use of DNA, e.g. a T-DNA on a binary plasmid, with a number of modified genes physically coupled to a second selectable marker gene. The advantage of this method is that the chimerical genes are physically coupled and therefore migrate as a single Mendelian locus.

B. Cross-pollination of transgenic plants each already capable of expressing one or more chimerical genes, preferably coupled to a selectable marker gene, with pollen from a transgenic plant which contains one or more chimerical genes coupled to another selectable marker. Afterwards the seed, which is obtained by this crossing, maybe selected on the basis of the presence of the two selectable markers, or on the basis of the presence of the chimerical genes themselves. The plants obtained from the selected seeds can afterwards be used for further crossing. In principle the chimerical genes are not on a single locus and the genes may therefore segregate as independent loci.

C. The use of a number of a plurality chimerical DNA molecules, e.g. plasmids, each having one or more chimerical genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second, (etc.), chimerical gene with new chimerical DNA, optionally comprising a selectable marker gene. As in method B, the chimerical genes are in principle not on a single locus and the chimerical genes may therefore segregate as independent loci.

E. Combinations of the above mentioned strategies.

The actual strategy may depend on several considerations as maybe easily determined such as the purpose of the parental lines (direct growing, use in a breeding program, use to produce hybrids) but is not critical with respect to the described invention.

It is known that practically all plants can be regenerated from cultured cells or tissues. The means for regeneration vary from species to species of plants, but generally a suspension of transformed protoplasts or a petri plate containing transformed explants is first provided. Shoots may be induced directly, or indirectly from callus via organogenesis or embryogenesis and subsequently rooted. Next to the selectable marker, the culture media will generally contain various amino acids and hormones, such as auxin and cytokinins. It is also advantageous to add glutamic acid and proline to the medium, especially for such species as corn and alfalfa. Efficient regeneration will depend on the medium, on the genotype and on the history of the culture. If these three variables are controlled regeneration is usually reproducible and repeatable.

After stable incorporation of the transformed gene sequences into the transgenic plants, the traits conferred by them can be transferred to other plants by sexual crossing. Any of a number of standard breeding techniques can be used, depending upon the species to be crossed.

The following examples are given only for purposes of illustration and do not intend to limit the scope of the invention.

Experimental Part
DNA Procedures

All DNA procedures were carried out according to standard methods described in Maniatis (Molecular Cloning, A laboratory Manual 2nd Edition, Cold Spring Harbor Laboratory, 1990).

Transformation of Arabidopsis

Transformation was carried out using co-cultivation of Arabidopsis thaliana (ecotype C24) root segments with Agrobacterium strain MOG101 containing a suitable binary vector as described by Valvekens et al. (1988, Proc. Nat. Acad. Sci. USA 85, 5536–5540) which is as follows:

Arabidopsis seeds were vernalized for 7 days at 4° C. before germination. Seeds were surface-sterilized for 2 min in 70% EtOH, transferred to 5% NaOCl/0.5 NaDodSO$_4$ for 15 min rinsed five times with sterile distilled water, and placed on 150×25 mm Petri dishes containing germination medium (GM) (Table 3) to germinate. Petri dishes were sealed with gas-permeable medical tape (Urgopore, Chenove France). Plants were grown at 22° C. in a 16-hr light/8-hr dark cycle. The same growth-room conditions were used for tissue culture procedures.

All plant media were buffered with 2-(N-morpholino) ethanesulfonic acid at 0.5 g/liter (pH 5.7: adjusted with 1 M KOH), solidified with 0.8% Difco Bacto agar, and autoclaved at 121° C. for 15 min. Hormones and antibiotics were dissolved in dimethyl sulfoxide and water, respectively, and were added to the medium after autoclaving and cooling to 65° C.

Intact roots were incubated for 3 days on solidified 0.5/0.05 medium (Table 3). Roots were then cut into small pieces of about 0.5 cm (herein referred to as "root explants") and transferred to 10 ml of liquid 0.5/0.05 medium; 0.5–1.0 ml of an overnight Agrobacterium culture was added. The root explants and bacteria were mixed by gentle shaking for about 2 min.

Subsequently, the root explants were blotted on sterile filter paper to remove most of the liquid medium and cocultivated for 48 hr on 0.5/0.05 agar. The explants were then rinsed in liquid 0.5/0.05 medium containing 1000 mg of vancomycin (Sigma) per liter. The pieces were blotted and then incubated on 0.15/5 agar (Table 3) supplemented with 750 mg of vancomycin and 50 mg of Km per liter. Three weeks after infection with agrobacteria containing a chimerical neo gene, green Km-resistant (Km$^R$) calli were formed in a background of yellowish root explants. At this point the root explants were transferred to fresh 0.15/5 agar containing only 500 mg of vancomycin and 50 mg of Km per liter. Three weeks later most green call had formed shoots. Transformed shoots were transferred to 150×25 mm Petri dishes containing GM to form roots or seeds or both. In these Petri dishes, many regenerants formed seeds without rooting. Rooted plants could also be transferred to soil to set seed. The following modification was made to obtain the initial root material 6 mg sterilized Arabidopsis thaliana C24 seeds were germinated in 50 ml GM (250 ml Erlenmeyer) on a rotary shaker (100 rpm) in a growth room for 9 days under low light conditions. Transgenic plants were regenerated from shoots grown on selection medium (50 mg/l kanamycin), rooted and transferred to germination medium or soil.

TABLE 3

| | PLANT MEDIA | | | | | |
|---|---|---|---|---|---|---|
| | | CIM | | | SIM | |
| | GM | R3* | PG1* | 0.5/0.05 | 0.05/7* | 0.15/5* |
| Salts + vitamins | MS | MS | B5 | B5 | MS | B5 |
| Sucrose, g/L | 10 | 30 | — | — | 30 | — |
| Glucose, g/L | — | — | 20 | 20 | — | 20 |
| IAA, mg/L | — | 5 | — | — | 0.05 | 0.15 |
| 2,4-D, mg/L | — | 0.5 | 2 | 0.5 | — | — |

TABLE 3-continued

PLANT MEDIA

|  | GM | CIM | | | SIM | |
|---|---|---|---|---|---|---|
|  |  | R3* | PG1* | 0.5/0.05 | 0.05/7* | 0.15/5* |
| 2ipAde, mg/L | — | — | — | — | 7 | 5 |
| Kin, mg/L | — | 0.3 | 0.05 | 0.05 | — | — |

L, liter; IAA, indole-3-acetic acid; Kin, kinetin; 2ipAde, N$^4$-(2-isopentenyl)adenine; CIM, callus-inducing medium; SIM, shoot-inducing medium; MS, Murashige & Skoog medium; B5, Gamborg B5 medium Transformation of Potato For the transformation of *Solanum tuberosum* var. Kardal a protocol as described in Hoekema et al. 1989 Bio/Technology 7, 273–278 was used with several modifications.

Peeled surface-sterilized potato tubers were cut in 2 mm thick slices. These were used to cut out disks of 1 cm in diameter around the periphery of the slice. The disks were collected in WM (Murashige & Skoog medium, containing 1 mg/l thiamine HCl, 0.5 mg/l pyridoxine HCl, 0.5 mg/l nicotinic acid, 100 mg/l myo-inositol, 30 g/l sucrose, 0.5 g/l MES pH 5.8). Inoculation with *Agrobacterium tumefaciens* strain EHA105 (Hood et al. 1993 Transgenic Research 2, 208–218) was done by replacing the WM with 100 ml fresh WM containing the resuspended pellet of 10 ml Agrobacterium culture grown freshly in LB+appropriate antibiotic to an $OD_{600}$ of 0.5–0.7. After incubating the tuber disks for 20 min in the bacterium suspension they were transferred to solidified CM (WM supplemented with 8 g/l agar, 3.5 mg/l zeatin riboside, 0.03 mg/l indole acetic acid) at a density of 20 explants/petridish. After two days the disks were transferred to PM (CM supplemented with 200 mg/l cefotaxime, 100 mg/l vancomycin) to select against the Agrobacteria. Three days later the disks were transferred to SIM plates (CM supplemented with 250 mg/l carbenicillin, 100 mg/l kanamycin) at a density of 10 explants/petridish to select for the regeneration of transformed shoots. After 2 weeks the tissue disks were transferred to fresh SIM, and after another 3 weeks they were transferred to SEM (SIM with 10×lower concentration of hormones). About 8–9 weeks after co-cultivation the shoots were large enough to cut them from the callus tissue and transfer them to glass tubes (Sigma, Cat. no. C5916) containing 10 ml of RM (WM containing 0.5×MS salts, 0.5×vitamins, 10 g/l sucrose, 100 mg/l cefotaxime, 50 mg/l vancomycin and 50 mg/l kanamycin) for rooting maintenance in vitro and vegetative propagation.

Handling of Nematodes, Growth and Infection of Plant Roots

Arabidopsis seeds were surface sterilized and sown in petri dishes (ø: 9 cm) on B5 medium containing 20 g/l glucose and 20 mg/l kanamycin. After 3 days at 4° C. the plates were incubated for 2 weeks in a growth chamber at 22° C. with 16-hr light/8 hr-dark cycle. Kanamycin-resistant plants were then transferred to soil-filled translucent plastic tubes (30×15×120 mm, Kelder plastibox b.v., The Netherlands). The tubes were placed tilted at an angle of 60 degrees to the vertical axis causing the roots to grow on the lower side of the tubes. This allows to monitor the infection process by eye and facilitates removal of the root system from the soil for GUS analysis. Infection was done after two more weeks by injecting a suspension containing 500 second stage larvae of *Heterodera schachtii* (in 3 ml $H_2O$) per root system or 300 second stage larvae of *Meloidogyne incognita* per root system into the soil.

Similarly, transformed potato shoots which had rooted on kanamycin-containing RM medium were transferred to soil-filled translucent plastic tubes (30×15×120 mm, Kelder plastibox b.v., The Netherlands) and grown tilted for another 2 weeks at 22° C. with 16 h light/8 h dark cycle. Infection was done by injecting a suspension containing 500 second stage larvae of *Globodera pallida* (in 3 ml $H_2O$) per root system into the soil.

GUS Assay

GUS activity was determined at various times during the infection process by thoroughly washing the root systems to remove most of the adhering soil and incubating them in X-Gluc solution (1 mg/ml X-Gluc, 50 nM $NaPO_4$ (pH7), 1 mM $K_4Fe(CN)_6$, 1 mM K $K_3Fe(CN)_6$, 10 mM EDTA, 0.1% Triton X100) at 37° C. over night. After removal of the chlorophyll from the tissue by incubation with 70% ethanol for several hours GUS staining was monitored under the microscope.

DNA Sequence Determination

Sequencing was done using standard techniques (Sanger et al., Proc. Natl. Acad. Sci. USA, 74, 5463–5467, 1977).

EXAMPLE 1

Construction of Binary Vector pMOG800

Figure 2:
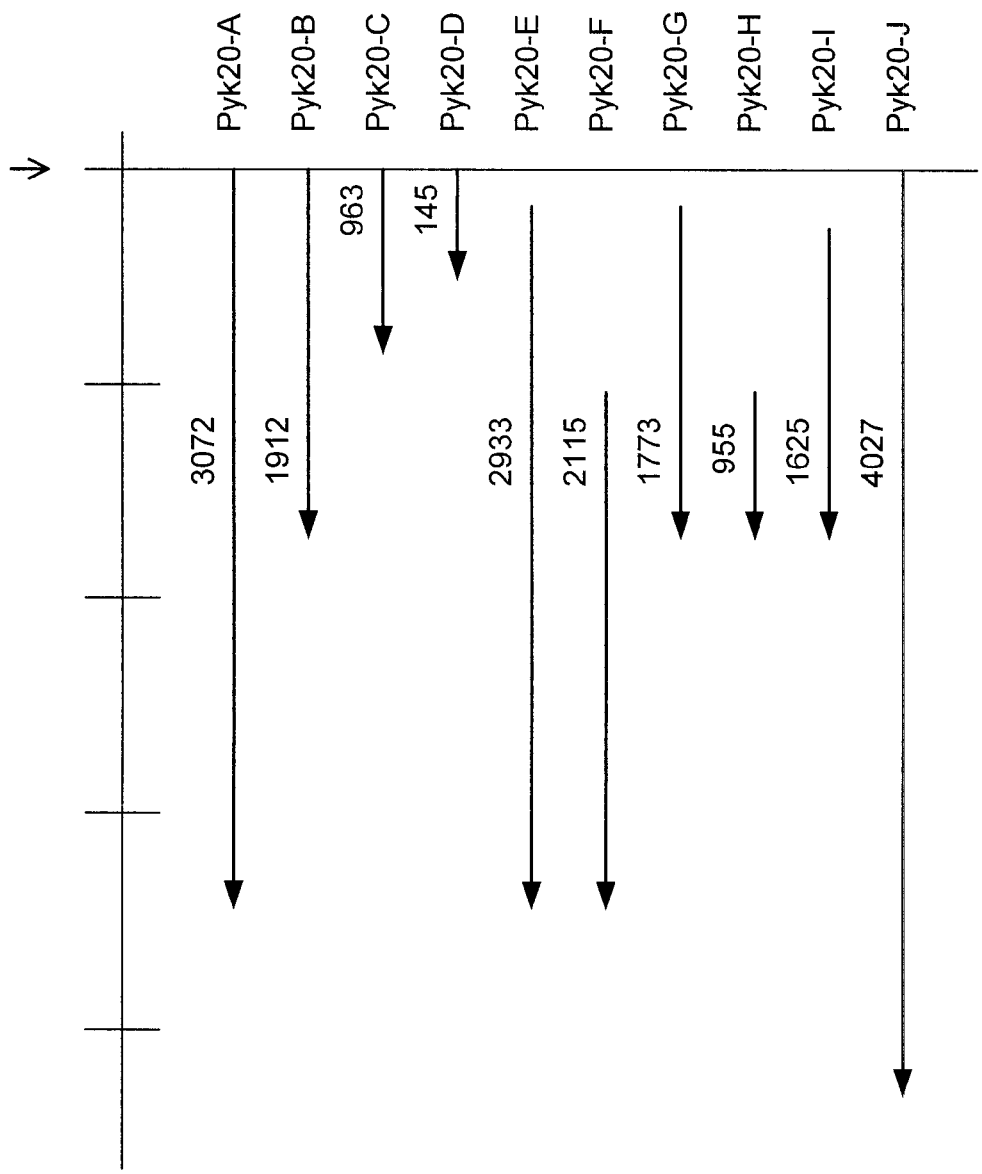
FIG. 2. Construction of transformation vectors with pyk20 promoter::gus fusion. The numbering is related to the length (in base pairs) of the promoter fragments. The start codon of the pyk20 gene is indicated with an arrowhead.

The binary vector pMOG800 is a derivative of pMOG23 (deposited at the Centraal Bureau voor schimmelcultures, Oosterstraat 1, Baarn, The Netherlands on Jan. 29, 1990 under number CBS 102.90) in which an additional KpnI restriction site was introduced into the polylinker between ScoRI and SmaI. This plasmid contains between the left and right borders of T-DNA a kanamycin resistance gene for selection of transgenic plant cells (FIG. 2). A sample of *E. coli* DH5 alpha, harboring pMOG800, was deposited at the Centraal Bureau voor Schimmelcultures, Oosterstraat 1, Baarn, The Netherlands, on Aug. 12, 1993 under number CBS 414.93.

EXAMPLE 2

Construction of Promoterless GUS Construct pMOG553

Construction of this vector is described in Goddijn et al. 1993 Plant J 4, 863–873. In this reference an error occurs; the construct contains a CaMV 35S RNA terminator behind the β-glucuronidase gene instead of the indicated nos terminator. The sequence between the T-DNA borders of this binary vector is available from the EMBL database under accession number: X84105. pMOGS553 carries the HygR marker for plant transformation.

EXAMPLE 3

Identification and Isolation of a Trapped NFS-preferential Promoter Fragment in *Arabidopsis thaliana*

The binary vector pMOG553 was mobilized by triparental mating to *Agrobacterium tumefaciens* strain MOG101 which is described in detail in WO 93/10251. The resulting strain was used for Arabidopsis root transformation. More than 1100 transgenic Arabidopsis plant lines were obtained in this way. Transgenic plants were grown to maturity, allowed to self-fertilize and the resulting seeds (S1) were harvested and vernalized. Subsequently S1 seeds were germinated on nutrient solution (Goddijn et al. 1993 Plant J 4, 863–873) solidified with 0.6% agar, 10 mg/l hygromycin and stored at 4° C. for a 4 day imbition period. At day 5 the plates were transferred to room temperature and moderate light (1000 lux, 16 h L/8 h D) for germination. Fourteen days old seedlings, resistant to hygromycin, were transferred to potting soil in tilted translucent plastic tubes (30×15×120 mm) for further growth at 5000 lux (20° C.). Growing the plants in this way causes most of the root system to grow on the lower side of the tubes in the interphase between soil and tube. After two weeks the roots were infected with nematodes as described in the Experimental part. At several time points after inoculation (ranging from 2–14 days), the root systems were analyzed for GUS activity as described in the Experimental part. Line pMOG553#884 was identified as a line which showed moderate GUS expression inside syncytia and giant cells induced by *Heterodera schachtii* and *Meloidogyne incognita*, respectively. In uninfected control plants (as well as in the infected plants) of this line weak GUS expression was detected in hydathodes and in the shoot apical meristem.

In line 884 this phenotype was found to segregate at a 1:3 ratio, indicating that the GUS construct is present at one locus per genome. The presence of only one T-DNA copy was confirmed by Southern analysis.

A 963 bp fragment of the trapped promoter sequence adjacent to the GUS open reading frame was isolated by inverse PCR. Genomic DNA of this line was cleaved with the restriction enzyme BstB I, which cleaves once in the GUS coding region, and religated. By subsequent digestion of the circular DNA with the enzyme SnaBI a linear fragment was obtained with known GUS sequences at the ends and the flanking plant sequence in between. This fragment was amplified using the primer set GUSinv5 (5' CTT TCC CAC CAA CGC TGA TC 3' SEQ ID NO: 5) and GUS13 (5' GTA CAG CGA AGA GGC AGT CAA CG 3' SEQ ID NO: 6), cloned in a multi-copy vector and sequenced (see below).

EXAMPLE 4

Identification of a Genomic Clone from wt Arabidopsis C24 Corresponding to the iPCR-amplified Plant Sequence In order to obtain a larger promoter fragment and to determine plant sequences downstream of the T-DNA insertion site a genomic library of Arabidopsis in lambda GEM11 (circa 300 000 recombinant phages) was screened with the inverse PCR fragment as probe. Restriction analysis of the resulting genomic clone revealed a 4.2 kb EcoRI fragment which hybridized to the iPCR probe. Sequencing of this genomic EcoRI fragment revealed that the 5' end of the T-DNA had inserted at the 3' end of this clone leaving 2964 bp of 5' sequence and 1236 bp 3' to the T-DNA insertion, as shown in SEQ ID NO: 1.

EXAMPLE 5

Construction of Promoterless GUS Construct pMOG819

This vector was constructed by cloning the GUS intron coding region (Vancanneyt et al. 1990, Mol. Gen. Genet. 220; 245–250) of pMOG553 as a BamHI-EcoRI fragment in the polylinker of pMOG800. The binary vector pMOG819 (FIG. 4) serves to introduce the cloned promoter fragments for further expression analysis after transformation of plants.

EXAMPLE 5A

Analysis of the Promoter Fragment after Re-introduction into Arabidopsis

Two kb of sequence 5' to the T-DNA insertion were subcloned in front of the GUS gene on the binary vector pMOG819. This was achieved by PCR amplification of this promoter fragment using the primers $C_{for}$ (5' TAC GCT CGA GAT CAC GAA AAT GTA TAT 3' SEQ ID NO: 7) and $C_{rev}$ (5' AGT ACC CGG GCT TTG GAT CGA CAA A 3' SEQ ID NO: 8). These primers introduced a flanking XhoI and SmaI site, respectively, which were used for subcloning in pMOG819. To determine the tissue-specific activity of the cloned promoter fragment the resulting construct C was mobilized to *Agrobacterium tumefaciens* and the corresponding strain was used to transform wildtype *Arabidopsis thaliana* plants. 44 Transformants were obtained. Seeds from the primary transformants were harvested and grown up for infection assays with *Heterodera schachtii* as described in the Experimental part. GUS analysis after nematode infection showed that 11% of the lines expressed the reporter gene in syncytia. In all of these lines GUS expression outside syncytia was virtually identical to the expression pattern found in the original tagged line, indicating that in principle all cis elements conferrirg tissue specificity were contained in the reintroduced promoter fragment.

EXAMPLE 6

Identification and Characterization of a cDNA Clone Corresponding to the Genomic Sequence 3' the T-DNA Insertion Site The genomic fragment contains several small potential open reading frames (ORFs). In order to determine if a functional gene is located in this region the most 3' 296 bp of the 4.2 kb EcoRI subfragment were isolated as HindIII/EcoRI fragment and used as probe to screen an Arabidopsis C24 cDNA library prepared from RNA of 14 days old plants. This screen revealed one hybridizing clone which was further analyzed by sequencing. The 491 bp 5' end of the cDNA was found to be identical to the 3' end of the genomic clone. RNA blot hybridization of this clone with RNA prepared from healthy leaf tissue, healthy root tissue and root tissue highly enriched for syncytia induced by *Heterodera schachtii* showed that the gene is expressed in leaves and in infected roots but not in healthy roots. This expression pattern corresponds to the GUS expression pattern found in tagged line pMOG553#884 suggesting that the plant regulatory sequence driving expression of the GUS reporter gene in the tagged line also regulates the plant gene corresponding to the identified cDNA.

EXAMPLE 7

Identification of Genomic Sequences Homologous to the 884-tagged cDNA in other Plants The cDNA clone was hybridized to genomic DNA from *Arabidopsis thaliana*, Sinapis alba cv. Albatros, *Brassica napus* L. var. napus cv. Akela, *Raphanus sativus* L. var. oleiformis cv. Silentina and Glycine max cv. Ronda, each digested with the restriction enzymes HindIII, EcoRI and BamHI. Whereas for the Arabidopsis genomic DNA only one genomic fragment was found homologous to the cDNA probe two to five weaker bands were found to cross-hybridize to the DNA of all other cruciferous plant species under moderately stringent washing conditions (1×SSC, 0.1% SDS incubation at 50° C.). No signal was detected in the soybean genomic DNA. These data suggest that related genes exist in other cruciferous plants.

EXAMPLE 8

Promoter Analysis Studies

The binary vector pMOG819 from Example 5 was used for engineering six different promoter::gus constructs.

C The 884 promoter::gus constructs −846/0 (A), −1610/0 (B) and −1990/o (C) were produced by PCR using oligonucleotide primers "A-reverse" (5'-GTTATCTAGATGGATCGTTAGTTGCA-3') (SEQ ID NO:9) in combination with the primer "ABC-forward" (5'-AGTACCCGGGCTTTGGATCGACAAA-3') (SEQ ID NO:8) for construct A, primer "B-reverse" (5'-AATTCTCGAGCGCCAAACTTTTAGTGA-3') (SEQ ID NO:10) in combination with the primer "ABC-forward" for construct B and primer "C-reverse" (5'-TACGCTCGAGATCACGAAAAT-GTATAT-3') (SEQ ID NO:7) in combination with the primer "ABC-forward" for construct C. The primers "A-reverse", "B-reverse" and "C-reverse" included the Xba I site and the primer "ABC-forward" included a Sma I site. After PCR with Pfu thermostable DNA polymerase (Stratagene GmbH, Heidelberg, Germany) the three products (A, B, C) were cut with Xba I and Sma I and cloned into pMOG819 at the corresponding sites.

Msp I/EcoR I (construct D), Tha I/EcoR I (construct E) and Tth111 I (construct F) restriction sites in the isolated 884 sequences were used to produce the constructs −2965/+116 (D), −2965/−54 (E) and −2469/−14 (F), respectively. The promoter fragments D, E and F were restricted from pBluescriptII KS (−) vector, blunt-ending with T4 DNA polymerase and cloned at the Sma I site of binary vector pMOG819.

The promoter constructs A–E in the binary vector pMOG819 were mobilized from *E. coli* DH5α into the *A. tumefaciens* strain MOG101 by triparental mating, using the helper plasmid pRK2013 in *E. coli* DH5α. Roots isolated from *A. thaliana* (ecotype C-24) were transformed, regenerated and selected.

Construct A gave a weak gus expression in hydathodes, but not in the nematode feeding site (NFS) and other tissues. Construct B triggered gus expression in hydathodes and in the apical merister of the shoot. The larger construct C gave gus expression in hydathodes, in the apical meristem of the shoot and, at a weak level, activity in the NFS. Construct D and construct E did not induce gus activity in the transformed plants. Plants transformed with construct F exhibited gus activity in the NFS similar to the plant line 884 suggesting that the sequence downstream and upstream of the region between −1999 and 0 bp (construct C) contained elements which are important for gus expression in the NFS.

EXAMPLE 9

Promoter Plasmid Constructions

The genomic clone harbouring the complete *A. thaliana* pyk20 promoter was used for engineering different promoter:: gus constructs (FIG. 3). All pyk20 promoter fragments were produced by PCR using oligonucleotide primers (see Table 4) including the Xba I site (for the reverse primers) and the Sma I site (for the forward primers). After PCR with Pfu thermostable DNA polymerase, the PCR products were cut with Xba I and Sma I and cloned into binary pMOG819 vector, between the gus gene and the left border of the T-DNA, at the corresponding sites.

TABLE 4

Primers of pyk20 promoter.

| Pyk20-A REV | GTTACTCGAGGTATCACGAAAATGT | (SEQ ID NO:11) |
| Pyk20-A FOR | CTCTCCCGGGCACTCACAATTCACA | (SEQ ID NO:12) |
| Pyk20-B REV | TAAGCTCGAGCGTAGTTGCATTTTA | (SEQ ID NO:13) |
| Pyk20-B FOR | CTCTCCCGGGCACTCACAATTCACA | (SEQ ID NO:14) |
| Pyk20-C REV | CATTCTCGAGGTTGGACCGGCTCTGTG | (SEQ ID NO:15) |
| Pyk20-C FOR | CTCTCCCGGGCACTCACAATTCACA | (SEQ ID NO:16) |
| Pyk20-D REV | GTGGCTCGAGTTTATTGAAGCTTATCG | (SEQ ID NO:17) |
| Pyk20-D FOR | CTCTCCCGGGCACTCACAATTCACA | (SEQ ID NO:18) |
| Pyk20-E REV | GTTACTCGAGGTATCACGAAAATGT | (SEQ ID NO:19) |
| Pyk20-E FOR | ACGACCCGGGTCAATAAAACAAACCCAC | (SEQ ID NO:20) |
| Pyk20-F REV | GTTACTCGAGGTATCACGAAAATGT | (SEQ ID NO:21) |
| Pyk20-F FOR | ACACCCCGGGGGTCCAACGTTTTTAATG | (SEQ ID NO:22) |
| Pyk20-G REV | TAAGCTCGAGCGTAGTTGCATTTTA | (SEQ ID NO:23) |
| Pyk20-G FOR | ACGACCCGGGTCAATAAAACAAACCCAC | (SEQ ID NO:24) |
| Pyk20-H REV | TAAGCTCGAGCGTAGTTGCATTTTA | (SEQ ID NO:25) |
| Pyk20-H FOR | ACACCCCGGGGGTCCAACGTTTTTAATG | (SEQ ID NO:26) |
| Pyk20-I REV | TAAGCTCGAGCGTAGTTGCATTTTA | (SEQ ID NO:27) |
| Pyk20-I FOR | GTTTCCCGGGTACTAATCGAGAAACA | (SEQ ID NO:28) |

TABLE 4-continued

Primers of pyk20 promoter.

| Pyk20-J REV | GAATTCTCGAGAAGACATGAGACAAT | (SEQ ID NO:29) |
|---|---|---|
| Pyk20-J FOR | CTCTCCCGGGCACTCACAATTCACA | (SEQ ID NO:30) |

Results

Expression of pyk20 promoter from seedling development to adult plants. The pattern of GUS staining of transgenic Arabidopsis plants that carried the pyk20-J::gus construct was followed after histochemical staining with X-Gluc at various developmental stages of the plant. Within 48 h of imbibition, GUS-specific, staining was observed in the entire embryo. Also on the third day, and fourth day, when cotyledons opened, staining was observed in roots and cotyledons. These staining patterns during early stages of plant development were similarly to plants transformed with constructs pyk20-A::gus and pyk20-B::gus.

On the seventh days after imbibition, GUS staining was detected in almost all tissues of the shoot and roots apart from differentiated tissues of hypocotyl. In the two week old plants high levels of GUS were observed in central rosette, in leaves and in roots, in particular, in vascular cylinder. The level of GUS activity was higher in older than in younger leaves. The overall pattern of GUS activity was observed in: central rosette >leaf>root. Histochemical analysis showed strong expression of pyk20-J::gus in meristematic tissue of apical root tips. In stems, GUS was localised in the vascular cylinder. The pyk20-J::gus fusion also exhibited a characteristic pattern of expression in floral organs. In all tested pyk20 promoter::gus constructs (A, B, J) the gus gene was up-regulated in NFS of *Heterodera schachtii*.

EXAMPLE 10

Expression of Pyk20-B::Gus Promoter Construct in an Heterologous System

The pattern of GUS staining of transgenic hairy roots of *Raphanus sativus* var. Siletina that carried the pyk20-B::gus construct was observed after histochemical staining with X-Gluc. The GUS was expressed in root tips and in root vascular tissue. In roots infected with Heterodera schachtii the GUS was observed also in NFS.

EXAMPLE 11

Construction of Pyk20-B Antisense Constructs

The 2.1 kb fragment encoding part of pyk20 cDNA clone was amplified using PCR. The PCR primers (Table 5) contained 20 nucleotides which were homologous to the amplified DNA fragment plus additional nucleotides to generate a Sma I (5' end of the construct) or a Cla I (3' end of the construct) site. After restriction of the PCR product with Cla I and Sma I the PCR fragment was directly subcloned in the antisense orientation in back of the pyk20 promoter B fragment. The pyk20-B::AS construct was introduced into *Agrobacterium tumefaciens* MOG101 by triparental mating with *E. coli* pRK2013 as helper strain. Verification of the integrity of the plasmids in Agrobacterium was achieved by Southern blotting of mini-prep DNA.

TABLE 5

Primers used for the PCR of antisense pyk20 gene construct.

| Primer | Sequences (5'→ 3') |
|---|---|
| AS-Pyk20 REV | TTTCCCGGGTTAAGACAAATTAAC (SEQ ID NO:31) |
| AS-Pyk20 FOR | TAGTATCGATACAAGCACTTTGGT (SEQ ID NO:32) |

---

SEQUENCE LISTING

```
<160> NUMBER OF SEQ ID NOS:  32

<210> SEQ ID NO 1
<211> LENGTH: 8302
<212> TYPE: DNA
<213> ORGANISM: Arabidopsis thaliana
<220> FEATURE:
<221> NAME/KEY: CDS
<222> LOCATION: (4038)..(4256)
<221> NAME/KEY: CDS
<222> LOCATION: (4807)..(5604)
<221> NAME/KEY: CDS
<222> LOCATION: (6777)..(6827)
<221> NAME/KEY: CDS
<222> LOCATION: (6919)..(7935)

<400> SEQUENCE: 1
gaattcaact caagacatga gacaatagat tcatgacaat atctactaca gtacttgcat      60
```

```
aacacaaatg taaactaact aacaattgat agtttagtac acaatccaaa ttgcaaaaga      120
gagatactgc aaatgatcta atcaaaactc atgcattcta cagttccata agacatttca      180
aatcactaat ctgaagaaat atgatgcatt aataacaaat atttgatgac taaacagaca      240
tttggatcag aaatgaagtt aaattaagca tttaattgct taataattta attgattgat      300
tccaaggcgt aataacacaa aattcttcgg gggaatttga agggatagag caaatcgctt      360
agggtaaaat gaaaacagcg ataagtaacg aattatcaaa gtctgagtta agaatcagga      420
aattgaggga ttgaagaaga ataaagggac ctggttcagg aggaattgag acgtgagtac      480
gctgtgttgg agaggacgac gtcattttcg ctcaaagcag cagattcagc aacggatgga      540
tgggtcttta ctctttgggc tgaagataac cgcaactaga ttcttcctga gttttttttt      600
cttttttgat aaaacgagag tccttacagg taaaaaccca ataaaaacca cgatccattt      660
ttatttggac atttaatatt taattatttt aaattagaaa ataattacac gaattattaa      720
attgtataat atgatattaa aaaattaagt gttattgatg tgttttcggt ctgactgtct      780
ataaaaaaaa tccacaacat aagagttgtt gttggagtca ttaaagagtc taatggtttg      840
tggtggtgtg accattagag gagggtttgt tgatgggtcg tgtgtttcac cattaacgtt      900
atcaaatggt tctcggttga ttggtcattt ttggagtcat caaatggctt atatgttacg      960
ctatgtatca cgaaaatgta tattttctc ctaaccatt cttcctttc caataatata      1020 gatttataaa ttcccgtgaa gataaatatg tggttttac ttttcgtttt tttcctatgt      1080
gaggagggtg ttattggttg ctaatttaca aggaattttg atgatttaa taatatcaca      1140 aaaagtaaat taagatttta aactattgct agggagtttt tttatgatct tgttgattag      1200
tttttcacag tcttgtaaag ttttcaaac aatctctcta ttttgatgat attttttac      1260 tttattttgt gaacaaaagt gtagaaaatc attaaacaat aacacaatat tttaattcat      1320
taacaatcat agtttttttt ttttaaattg ataacgccaa actttagtga ctttataatt      1380
ttttaattat aaggtaagtc tcctaagata tatgttttgg gttaaagtat tcacaatgtc      1440
caccatgtta tgtgatatat taccccatgt atattcattt tgtcatttaa tcttacctttt      1500 ttgcattttt gtttggctta aaatctacaa tatctttta ctattaaaaa acctgtaata      1560
ttcatttaca aatcaatatt ttattctttt tagacatatc ctatttaat ttctacattc      1620 ttttcaaaat agttactaaa ataattgtt tctaaaagcc atgaatataa cacaacaact      1680
aatcaatctc cacaatatat attatatata ttaacaaaaa gtgtattggt gataaaaagt      1740
acttgatgat acactaaaca aaaggataa atgggagaat ttttattttt gaaagatgaa      1800
acattttagg ttatatattt catgacccctt ataataaaa ttcctggctc caccactgga      1860
tatctctaca tatttccaac atcaatatcc attgatattt gataatcttt accaaaaatt      1920
cgcaatctcc tttagagtga aagcgagtat aaccgtatga ccaaactatt tcgagtacca      1980
ttggtaattc cttaccttaa gcttccagag gtattagtgc tatatattca tagtgccacc      2040
gagtattttg aactccgaaa tgatttctca ctatccgacc actcccaatt atataacatg      2100
cttagaatta ttcgtaagat ggatcgtagt tgcatttac gacaccatac aggacaagtc      2160
catgatagtt tgagttggtg gattttggaa cccctgcaaa tttatttat acataacaaa      2220 ggccccaatc cattccttag catcacaact tgggacttct atcttttgaa ggatacattc      2280
acttgttggt tttggtaaat atgattgttt ctttacttcc gaataagcaa taaataaaag      2340
tatctaaaaa cggaagtaac ttttgatgat cctaaaggtt ttgtaattga tacatgtcca      2400
```

-continued

```
aaaacctctt aatattctct ctcacaaact gttgatggag ttaacaaagg gagacaaggt    2460
aattgggaca atatcaacgt taggtacagg acaagtgaaa aatgtggggt tgatgtcttc    2520
agctgcagca tatcacccgt tggtatatat tgtcaattat tagtcctatg gatttgaaac    2580
gtgttttagt aaataagagt gtccaagtgg gacatttcca ataacgtatc acagctccta    2640
gagcttttgc tatgtttctc taggcctggg cgcctagccc acattccaag caaggaaatg    2700
aatggagttg ggcatcaaaa ttttggaagc attttttaaga caaattatct tttaagtttc    2760
cttttttaaa cataaactat attttaggct tttttaagat aaatattatt tgggtttcct    2820
ttcactcata tttttggatt ttaacttaac aaaacatagg gcgtgtctat ttgactccac    2880
ctaccctact ggagttcgat cccactaaat cgcgttatcc cgtatagtag ggattgacta    2940
tggatcggac tttgtcgatc caaagatatc taagaaattc agaaaagatt gtataaaatt    3000
cagaaacgat tttacgaaat tcatgaaaaa tgagaaatac atgtttttt taatttacgt    3060 cggcattaaa aacgttggac cggctctgtg tttcgccaaa gaaattgttt cagtttatgc    3120
atgatcttca acttcatatt cttgttttca attctggaaa tccctaacag atcggagctc    3180
tcctcattca gtgagttgga agattgcatg attatataat tactcttcac atccacatat    3240
attacattat attcccctat aatttcatac aaccctagaa aagaatcttc aagtaatcta    3300
atcgtgtcga tgactccact catttgctag aaaagaaaaa acaaacagac ttcatttagc    3360
tgaaaacaat cttttattca acattataaa gcactgatca agaacctct aacatggtaa    3420 tatatctatg acattttacg tatcctaaaa gaaaacaaaa agtgatgtat tggatgatgt    3480
tttttttttt ttactttcta gtttcttatt acaacgacaa aaagagtcca cgtcgtcacg    3540
cactttccgg tggtgaaaaa atgtccaaat ggattaaatc tataatatct ccagagagat    3600
cctctccttc tatcttttg ggctccactt ttcctatctc tttttgcccc tttcctctct    3660
ctgttcacaa gtcatcttct tccttcctct gaatcttgtt cctttttgct ctctctactt    3720
gattcaccca ctctgttttc tcgattagta cgttgaaaac tcactttggt tttgtttgat    3780
tcctctttag tctgtttttc tgatttcgtt ttctctgatt ggtttggtgg tgagatctct    3840
atcgtagttt gtcctttggg ttaagatatt tcatttgatt ggtgggtttg ttttattgaa    3900
gcttatcgtt gtgaaagttg gagtctttct cagttttag gttgaattat taagagaaag    3960
ggaagatttt tggtgtgaag ttaggttatt tggggtttga gaagtttgca agtgaaaaag    4020
gttgtgaatt gtgagtg atg aag aga ggg aaa gat gag gag aag ata ttg      4070
                    Met Lys Arg Gly Lys Asp Glu Glu Lys Ile Leu
                     1               5                  10 gaa cct atg ttt cct cgg ctt cat gtg aat gat gca gat aaa gga ggg    4118
Glu Pro Met Phe Pro Arg Leu His Val Asn Asp Ala Asp Lys Gly Gly
         15                  20                  25 cct aga gct cct cct aga aac aag atg gct ctt tat gag cag ctt agt    4166
Pro Arg Ala Pro Pro Arg Asn Lys Met Ala Leu Tyr Glu Gln Leu Ser
     30                  35                  40 att cct tct cag agg ttt ggt gat cat gga acc agg aat tct cgt agt    4214
Ile Pro Ser Gln Arg Phe Gly Asp His Gly Thr Arg Asn Ser Arg Ser
 45                  50                  55 aac aac aca agc act ttg gtt cat cct gga cca tct agt cag            4256
Asn Asn Thr Ser Thr Leu Val His Pro Gly Pro Ser Ser Gln
 60                  65                  70 gtattgtttt gattttgatc attgtatagg ctcttgatgt tattagttgt atgagtttgg    4316
atgttatata gcctgaaaga gaaagtagga cattggttga tctatgtttc aattgttatc    4376
agatcatagt atcttctttt tgcttatgga ttgagctttt aggattgaat tctcctgtat    4436
```

```
atatgagagt cttgtagaca caagtttatc taagtgtggt ttatttctta aaactaacat    4496
tcttgttgtg cctgattctt tttatgttct gaagttcgat gaaagttctt gtgattgccc    4556
tgagcattca gatcatagta tcttcttttt gcttatggat tgagctttta ggattgaatc    4616
tcctgtatat atgagagtct tgtagacaca agtttatcta agtgtggttt atttcttaaa    4676
actaacattc ttgttgtgcc tgattctttt tatgttctga agttcgatga agtttcttg     4736 tgattgccct gagcattcag actattgcaa ggacatgaga ataatccctt ttttaccctc    4796
```

```
ttcaatgcag cct tgt ggt gtg gaa aga aac tta tct gtc cag cat ctt       4845
           Pro Cys Gly Val Glu Arg Asn Leu Ser Val Gln His Leu
                75                  80                  85 gat tct tca gcc gca aac caa gca act gag aag ttt gtc tcc caa atg      4893
Asp Ser Ser Ala Ala Asn Gln Ala Thr Glu Lys Phe Val Ser Gln Met
         90                  95                 100 tcc ttc atg gaa aat gtg aga tct tcg gca cag cat gat cag agg aaa      4941
Ser Phe Met Glu Asn Val Arg Ser Ser Ala Gln His Asp Gln Arg Lys
        105                 110                 115 atg gtg aga gag gaa gaa gat ttt gca gtt cca gta tat att aac tca      4989
Met Val Arg Glu Glu Glu Asp Phe Ala Val Pro Val Tyr Ile Asn Ser
    120                 125                 130 aga aga tct cag tct cat ggc aga acc aag agt ggt att gag aag gaa      5037
Arg Arg Ser Gln Ser His Gly Arg Thr Lys Ser Gly Ile Glu Lys Glu
135                 140                 145                 150 aaa cac acc cca atg gtg gca cct agc tct cat cac tcc att cga ttt      5085
Lys His Thr Pro Met Val Ala Pro Ser Ser His His Ser Ile Arg Phe
                155                 160                 165 caa gaa gtg aat cag aca ggc tca aag caa aac gta tgt ttg gct act      5133
Gln Glu Val Asn Gln Thr Gly Ser Lys Gln Asn Val Cys Leu Ala Thr
            170                 175                 180 tgt tca aaa cct gaa gtt agg gat cag gtc aag gcg aat cga agg tca      5181
Cys Ser Lys Pro Glu Val Arg Asp Gln Val Lys Ala Asn Arg Arg Ser
        185                 190                 195 ggt ggc ttt gta atc tct tta gat gta tca gtc aca gag gag att gat      5229
Gly Gly Phe Val Ile Ser Leu Asp Val Ser Val Thr Glu Glu Ile Asp
    200                 205                 210 ctc gaa aaa tca gca tca agt cat gat aga gta aat gat tat aat gct      5277
Leu Glu Lys Ser Ala Ser Ser His Asp Arg Val Asn Asp Tyr Asn Ala
215                 220                 225                 230 tcc ttg aga caa gag tct aga aat cgg tta tac cga gat ggt ggc aaa      5325
Ser Leu Arg Gln Glu Ser Arg Asn Arg Leu Tyr Arg Asp Gly Gly Lys
                235                 240                 245 act cgt ctg aag gac act gat aat gga gct gaa tct cac ttg gca acg      5373
Thr Arg Leu Lys Asp Thr Asp Asn Gly Ala Glu Ser His Leu Ala Thr
            250                 255                 260 gaa aat cat tca caa gag ggt cat ggc agt cct gaa gac att gat aat      5421
Glu Asn His Ser Gln Glu Gly His Gly Ser Pro Glu Asp Ile Asp Asn
        265                 270                 275 gat cgt gaa tac agc aaa agc aga gca tgc gcc tct ctg cag cag ata      5469
Asp Arg Glu Tyr Ser Lys Ser Arg Ala Cys Ala Ser Leu Gln Gln Ile
    280                 285                 290 aat gaa gag gca agt gat gac gtt tct gat gat tcg atg gtg gat tct      5517
Asn Glu Glu Ala Ser Asp Asp Val Ser Asp Asp Ser Met Val Asp Ser
295                 300                 305                 310 ata tcc agc ata gat gtc tct ccc gat gat gtt gtg ggt ata tta ggt      5565
Ile Ser Ser Ile Asp Val Ser Pro Asp Asp Val Val Gly Ile Leu Gly
                315                 320                 325 caa aaa cgt ttc tgg aga gca agg aaa gcc att gcc aag taagttcact       5614
Gln Lys Arg Phe Trp Arg Ala Arg Lys Ala Ile Ala Lys
```

-continued

```
              330                    335
agaaatttac agtttggtta tttattctcc gctctttcta tttatctcct tctttgatac    5674
caacattttt tgcttgaaag aagttaatat ttaagcattg ttccgtagtc ttactgaagc    5734
tttttcctct gttgttttt gctatttca ttgaggactg tggtagggca tatttcacta    5794
tcaccaaatt tcaaattcta gaacactctc cttcatattt ttttcatgat taatgctgca    5854
attgatgcga tatacatata tgactataac tcagtttcat attctgtctc attttgggag    5914
aagagatttc aggtttatgc ttgagaagtg atggttctat agttgagagg ccctgattc    5974 atctaaaatg gtcctattat gtgtttagtt gtagagtcct cggtagaata ttaacgcgtt    6034
taacacgttg gatcatgtta tagcaggggg gacattctct gttgacctat attgtgcaag    6094
gtgcccgccg atggctttat tactatacct tctttgcatc tggttgttgg aacatgtccc    6154
tgtctcggtt tggtattgct tttattctgc actgtcgtct tgggcatttt ccctacttgt    6214
cattcaaggg gttgaaccag gtagggaaat gtttttccga ggaccccagg atctaaattt    6274
tagttaacca tacgtaaagt tagttttgag tcttatgacg atgcagaatt atagtttctt    6334
cttactactg cttaagagga tccttagtgt ggttgtgaac tacagagttt ttatgattat    6394
aggcttcatg acttaacttt taaggttcaa tgtactctaa tccatatggt aaggtatcgg    6454
attcacgacc atgccaatat aagattttta ttttcttgct tcttgttaaa tatctgacat    6514
ctcattttgc agagtataag tgcgctgtaa gctagatttc aataagcccg tcctttgcat    6574
tgttatctat gctttaatat gtcattggac ccattgattt ggttttcttc tatcttttt    6634 gattggctat gtattcttgt ttctttttc ctatctcatt cgatcgtatt gttccattag    6694
ctgttcaacc taaactatgt ctctctttgt tgaacttttg atggataatc ttcttatatg    6754
tgactctgtt tctcattaca gt caa caa aga gta ttt gct gtt caa cta ttt    6806
                        Gln Gln Arg Val Phe Ala Val Gln Leu Phe
                                340                 345 gag ttg cac aga ctg att aag gtaaaagtca ttcaagaact tctcatatgt          6857
Glu Leu His Arg Leu Ile Lys
350             355 ttccatgagt atttgtttct ctcgagcgt gaaaaaacct cttcaactgt gtaataatca    6917 g gtt caa aaa ctt att gct gca tca ccg gat ctc ttg ctc gat gag atc    6966
  Val Gln Lys Leu Ile Ala Ala Ser Pro Asp Leu Leu Leu Asp Glu Ile
                360                 365                 370 agt ttt ctt gga aaa gtt tct gct aaa agc tat cca gtg aag aag ctc      7014
Ser Phe Leu Gly Lys Val Ser Ala Lys Ser Tyr Pro Val Lys Lys Leu
        375                 380                 385 ctt cca tca gaa ttt ctg gta aag cct cct cta cca cat gtt gtc gtc      7062
Leu Pro Ser Glu Phe Leu Val Lys Pro Pro Leu Pro His Val Val Val
    390                 395                 400 aaa caa agg ggt gac tcg gag aag act gac caa cat aaa atg gaa agc      7110
Lys Gln Arg Gly Asp Ser Glu Lys Thr Asp Gln His Lys Met Glu Ser
405                 410                 415                 420 tca gct gag aac gta gtt ggg agg ttg tca aat caa ggt cat cat caa      7158
Ser Ala Glu Asn Val Val Gly Arg Leu Ser Asn Gln Gly His His Gln
                425                 430                 435 cat cca act aca tgc ctt ttc cag caa aca acc cac cgg ctt cac cgg      7206
His Pro Thr Thr Cys Leu Phe Gln Gln Thr Thr His Arg Leu His Arg
            440                 445                 450 ctc caa atg gat att gct ttc ctc ctc agc ctc ctc ctt cag gaa atc      7254
Leu Gln Met Asp Ile Ala Phe Leu Leu Ser Leu Leu Leu Gln Glu Ile
        455                 460                 465 atc agc aat ggt gat ccc tgt aat gtc tcc ctc gga agg act gat ata      7302
```

```
Ile Ser Asn Gly Asp Pro Cys Asn Val Ser Leu Gly Arg Thr Asp Ile
    470                 475                 480 cag cct cac cca ggt atg gca cac acg ggg cat tat gga gga tat tat      7350
Gln Pro His Pro Gly Met Ala His Thr Gly His Tyr Gly Gly Tyr Tyr
485                 490                 495                 500 ggt cat tat atg cct aca cca atg gta atg cct caa tat cac ccc ggc      7398
Gly His Tyr Met Pro Thr Pro Met Val Met Pro Gln Tyr His Pro Gly
                505                 510                 515 atg gga ttc cca cct cct ggt aat ggc tac ttc cct cca tat gga atg      7446
Met Gly Phe Pro Pro Pro Gly Asn Gly Tyr Phe Pro Pro Tyr Gly Met
                520                 525                 530 atg ccc acc ata atg aac cca tat tgt tca agc caa caa caa caa caa      7494
Met Pro Thr Ile Met Asn Pro Tyr Cys Ser Ser Gln Gln Gln Gln Gln
            535                 540                 545 caa caa ccc aat gag caa atg aac cag ttt gga cat cct gga aat ctt      7542
Gln Gln Pro Asn Glu Gln Met Asn Gln Phe Gly His Pro Gly Asn Leu
550                 555                 560 cag aac acc caa caa caa caa cag aga tct gat aat gaa cct gct cca      7590
Gln Asn Thr Gln Gln Gln Gln Gln Arg Ser Asp Asn Glu Pro Ala Pro
565                 570                 575                 580 cag caa cag caa cag cca aca aag tct tat ccg cga gca aga aag agc      7638
Gln Gln Gln Gln Gln Pro Thr Lys Ser Tyr Pro Arg Ala Arg Lys Ser
                585                 590                 595 agg caa ggg agc aca gga agc agt cca agt ggg cca cag gga atc tct      7686
Arg Gln Gly Ser Thr Gly Ser Ser Pro Ser Gly Pro Gln Gly Ile Ser
                600                 605                 610 ggt agc aag tcc ttt ggg cca ttc gca gcc gtt gat gag gac agc aac      7734
Gly Ser Lys Ser Phe Gly Pro Phe Ala Ala Val Asp Glu Asp Ser Asn
            615                 620                 625 atc aac aat gca cct gag caa acg atg aca aca acc aca acg acg aca      7782
Ile Asn Asn Ala Pro Glu Gln Thr Met Thr Thr Thr Thr Thr Thr Thr
630                 635                 640 aga aca act gtt act cag aca aca aga gat ggg gga gga gtg acg aga      7830
Arg Thr Thr Val Thr Gln Thr Thr Arg Asp Gly Gly Gly Val Thr Arg
645                 650                 655                 660 gtg ata aag gtg gta cct cac aac gca aag ctc gcg agt gag aat gct      7878
Val Ile Lys Val Val Pro His Asn Ala Lys Leu Ala Ser Glu Asn Ala
                665                 670                 675 gcc agg att ttc cag tca ata caa gaa gaa cgt aaa cgc tat gac tcc      7926
Ala Arg Ile Phe Gln Ser Ile Gln Glu Glu Arg Lys Arg Tyr Asp Ser
            680                 685                 690 tct aag cct taatcctctc tatgcgtatt gtacttgata tgttttttac              7975
Ser Lys Pro
        695 aaaattagaa aaattgtgat agatgttatc ctcaatatac gtaccatgta aacgtattat    8035 ggtataagcc tcatttatat gtgttaattt gtcttaaagc cttgaaatca cttgaacaac    8095 aaagattatt tgaaacaact acttacaatc actgtttctt ttgtctgtga catcaagaac    8155 ttaagcatac catatttaca acatcgttgt ctacatggga aggagtataa ttggtagtaa    8215 gatattaatg gacatcgatt aatataggc ggagacgaag tcaagcactg aatccacggt     8275 cagacggctc aattgcctat agtgagt                                        8302

<210> SEQ ID NO 2
<211> LENGTH: 695
<212> TYPE: PRT
<213> ORGANISM: Arabidopsis thaliana

<400> SEQUENCE: 2
```

-continued

```
Met Lys Arg Gly Lys Asp Glu Glu Lys Ile Leu Glu Pro Met Phe Pro
 1               5                  10                  15

Arg Leu His Val Asn Asp Ala Asp Lys Gly Gly Pro Arg Ala Pro Pro
             20                  25                  30

Arg Asn Lys Met Ala Leu Tyr Glu Gln Leu Ser Ile Pro Ser Gln Arg
         35                  40                  45

Phe Gly Asp His Gly Thr Arg Asn Ser Arg Ser Asn Asn Thr Ser Thr
     50                  55                  60

Leu Val His Pro Gly Pro Ser Ser Gln Pro Cys Gly Val Glu Arg Asn
 65                  70                  75                  80

Leu Ser Val Gln His Leu Asp Ser Ser Ala Ala Asn Gln Ala Thr Glu
             85                  90                  95

Lys Phe Val Ser Gln Met Ser Phe Met Glu Asn Val Arg Ser Ser Ala
         100                 105                 110

Gln His Asp Gln Arg Lys Met Val Arg Glu Glu Asp Phe Ala Val
     115                 120                 125

Pro Val Tyr Ile Asn Ser Arg Arg Ser Gln Ser His Gly Arg Thr Lys
 130                 135                 140

Ser Gly Ile Glu Lys Glu Lys His Thr Pro Met Val Ala Pro Ser Ser
145                 150                 155                 160

His His Ser Ile Arg Phe Gln Glu Val Asn Gln Thr Gly Ser Lys Gln
             165                 170                 175

Asn Val Cys Leu Ala Thr Cys Ser Lys Pro Glu Val Arg Asp Gln Val
         180                 185                 190

Lys Ala Asn Arg Arg Ser Gly Gly Phe Val Ile Ser Leu Asp Val Ser
     195                 200                 205

Val Thr Glu Glu Ile Asp Leu Glu Lys Ser Ala Ser Ser His Asp Arg
 210                 215                 220

Val Asn Asp Tyr Asn Ala Ser Leu Arg Gln Glu Ser Arg Asn Arg Leu
225                 230                 235                 240

Tyr Arg Asp Gly Gly Lys Thr Arg Leu Lys Asp Thr Asp Asn Gly Ala
             245                 250                 255

Glu Ser His Leu Ala Thr Glu Asn His Ser Gln Glu Gly His Gly Ser
         260                 265                 270

Pro Glu Asp Ile Asp Asn Asp Arg Glu Tyr Ser Lys Ser Arg Ala Cys
     275                 280                 285

Ala Ser Leu Gln Gln Ile Asn Glu Glu Ala Ser Asp Val Ser Asp
     290                 295                 300

Asp Ser Met Val Asp Ser Ile Ser Ser Ile Asp Val Ser Pro Asp Asp
305                 310                 315                 320

Val Val Gly Ile Leu Gly Gln Lys Arg Phe Trp Arg Ala Arg Lys Ala
             325                 330                 335

Ile Ala Lys Gln Gln Arg Val Phe Ala Val Gln Leu Phe Glu Leu His
         340                 345                 350

Arg Leu Ile Lys Val Gln Lys Leu Ile Ala Ala Ser Pro Asp Leu Leu
     355                 360                 365

Leu Asp Glu Ile Ser Phe Leu Gly Lys Val Ser Ala Lys Ser Tyr Pro
 370                 375                 380

Val Lys Lys Leu Leu Pro Ser Glu Phe Leu Val Lys Pro Pro Leu Pro
385                 390                 395                 400

His Val Val Lys Gln Arg Gly Asp Ser Glu Lys Thr Asp Gln His
             405                 410                 415

Lys Met Glu Ser Ser Ala Glu Asn Val Val Gly Arg Leu Ser Asn Gln
```

-continued

```
                  420                 425                 430
Gly His His Gln His Pro Thr Thr Cys Leu Phe Gln Gln Thr Thr His
            435                 440                 445
Arg Leu His Arg Leu Gln Met Asp Ile Ala Phe Leu Leu Ser Leu Leu
    450                 455                 460
Leu Gln Glu Ile Ile Ser Asn Gly Asp Pro Cys Asn Val Ser Leu Gly
465                 470                 475                 480
Arg Thr Asp Ile Gln Pro His Pro Gly Met Ala His Thr Gly His Tyr
                485                 490                 495
Gly Gly Tyr Tyr Gly His Tyr Met Pro Thr Pro Met Val Met Pro Gln
            500                 505                 510
Tyr His Pro Gly Met Gly Phe Pro Pro Gly Asn Gly Tyr Phe Pro
    515                 520                 525
Pro Tyr Gly Met Met Pro Thr Ile Met Asn Pro Tyr Cys Ser Ser Gln
530                 535                 540
Gln Gln Gln Gln Gln Pro Asn Glu Gln Met Asn Gln Phe Gly His
545                 550                 555                 560
Pro Gly Asn Leu Gln Asn Thr Gln Gln Gln Gln Arg Ser Asp Asn
                565                 570                 575
Glu Pro Ala Pro Gln Gln Gln Gln Pro Thr Lys Ser Tyr Pro Arg
            580                 585                 590
Ala Arg Lys Ser Arg Gln Gly Ser Thr Gly Ser Ser Pro Ser Gly Pro
    595                 600                 605
Gln Gly Ile Ser Gly Ser Lys Ser Phe Gly Pro Phe Ala Ala Val Asp
    610                 615                 620
Glu Asp Ser Asn Ile Asn Asn Ala Pro Glu Gln Thr Met Thr Thr Thr
625                 630                 635                 640
Thr Thr Thr Thr Arg Thr Thr Val Thr Gln Thr Thr Arg Asp Gly Gly
                645                 650                 655
Gly Val Thr Arg Val Ile Lys Val Val Pro His Asn Ala Lys Leu Ala
            660                 665                 670
Ser Glu Asn Ala Ala Arg Ile Phe Gln Ser Ile Gln Glu Glu Arg Lys
    675                 680                 685
Arg Tyr Asp Ser Ser Lys Pro
    690                 695
```

<210> SEQ ID NO 3
<211> LENGTH: 2606
<212> TYPE: DNA
<213> ORGANISM: Arabidopsis thaliana
<220> FEATURE:
<221> NAME/KEY: CDS
<222> LOCATION: (328)..(2412)

<400> SEQUENCE: 3

```
ctctctctac ttgattcacc cactctgttt ctcgattagt acgttgaaaa ctcactttgg   60
ttttgtttga ttcctcttta gtctgttttt cgatttcgtt ttctctgatt ggtttggtgg   120
tgagatctct atcgtagttt gtcctttggg ttaagatatt tcatttgatt ggtgggtttg   180
ttttattgaa gcttatcgtt gtgaaagttg gagtctttct cagttttttag gttgaattat   240
taagagaaag ggaagatttt tggtgtgaag ttaggttatt tggggtttga gaagtttgca   300
agtgaaaaag gttgtgaatt gtgagtg atg aag aga ggg aaa gat gag gag aag   354
                            Met Lys Arg Gly Lys Asp Glu Glu Lys
                              1               5
ata ttg gaa cct atg ttt cct cgg ctt cat gtg aat gat gca gat aaa   402
```

```
Ile Leu Glu Pro Met Phe Pro Arg Leu His Val Asn Asp Ala Asp Lys
 10                  15                  20                  25 gga ggg cct aga gct cct cct aga aac aag atg gct ctt tat gag cag       450
Gly Gly Pro Arg Ala Pro Pro Arg Asn Lys Met Ala Leu Tyr Glu Gln
             30                  35                  40 ctt agt att cct tct cag agg ttt ggt gat cat gga acc agg aat tct       498
Leu Ser Ile Pro Ser Gln Arg Phe Gly Asp His Gly Thr Arg Asn Ser
             45                  50                  55 cgt agt aac aac aca agc act ttg gtt cat cct gga cca tct agt cag       546
Arg Ser Asn Asn Thr Ser Thr Leu Val His Pro Gly Pro Ser Ser Gln
             60                  65                  70 cct tgt ggt gtg gaa aga aac tta tct gtc cag cat ctt gat tct tca       594
Pro Cys Gly Val Glu Arg Asn Leu Ser Val Gln His Leu Asp Ser Ser
 75                  80                  85 gcc gca aac caa gca act gag aag ttt gtc tcc caa atg tcc ttc atg       642
Ala Ala Asn Gln Ala Thr Glu Lys Phe Val Ser Gln Met Ser Phe Met
 90                  95                 100                 105 gaa aat gtg aga tct tcg gca cag cat gat cag agg aaa atg gtg aga       690
Glu Asn Val Arg Ser Ser Ala Gln His Asp Gln Arg Lys Met Val Arg
                110                 115                 120 gag gaa gaa gat ttt gca gtt cca gta tat att aac tca aga aga tct       738
Glu Glu Glu Asp Phe Ala Val Pro Val Tyr Ile Asn Ser Arg Arg Ser
             125                 130                 135 cag tct cat ggc aga acc aag agt ggt att gag aag gaa aaa cac acc       786
Gln Ser His Gly Arg Thr Lys Ser Gly Ile Glu Lys Glu Lys His Thr
         140                 145                 150 cca atg gtg gca cct agc tct cat cac tcc att cga ttt caa gaa gtg       834
Pro Met Val Ala Pro Ser Ser His His Ser Ile Arg Phe Gln Glu Val
     155                 160                 165 aat cag aca ggc tca aag caa aac gta tgt ttg gct act tgt tca aaa       882
Asn Gln Thr Gly Ser Lys Gln Asn Val Cys Leu Ala Thr Cys Ser Lys
170                 175                 180                 185 cct gaa gtt agg gat cag gtc aag gcg aat cga agg tca ggt ggc ttt       930
Pro Glu Val Arg Asp Gln Val Lys Ala Asn Arg Arg Ser Gly Gly Phe
             190                 195                 200 gta atc tct tta gat gta tca gtc aca gag gag att gat ctc gaa aaa       978
Val Ile Ser Leu Asp Val Ser Val Thr Glu Glu Ile Asp Leu Glu Lys
             205                 210                 215 tca gca tca agt cat gat aga gta aat gat tat aat gct tcc ttg aga      1026
Ser Ala Ser Ser His Asp Arg Val Asn Asp Tyr Asn Ala Ser Leu Arg
         220                 225                 230 caa gag tct aga aat cgg tta tac cga gat ggt ggc aaa act cgt ctg      1074
Gln Glu Ser Arg Asn Arg Leu Tyr Arg Asp Gly Gly Lys Thr Arg Leu
 235                 240                 245 aag gac act gat aat gga gct gaa tct cac ttg gca acg gaa aat cat      1122
Lys Asp Thr Asp Asn Gly Ala Glu Ser His Leu Ala Thr Glu Asn His
 250                 255                 260                 265 tca caa gag ggt cat ggc agt cct gaa gac att gat aat gat cgt gaa      1170
Ser Gln Glu Gly His Gly Ser Pro Glu Asp Ile Asp Asn Asp Arg Glu
             270                 275                 280 tac agc aaa agc aga gca tgc gcc tct ctg cag cag ata aat gaa gag      1218
Tyr Ser Lys Ser Arg Ala Cys Ala Ser Leu Gln Gln Ile Asn Glu Glu
             285                 290                 295 gca agt gat gac gtt tct gat gat tcg atg gtg gat tct ata tcc agc      1266
Ala Ser Asp Asp Val Ser Asp Asp Ser Met Val Asp Ser Ile Ser Ser
         300                 305                 310 ata gat gtc tct ccc gat gat gtt gtg ggt ata tta ggt caa aaa cgt      1314
Ile Asp Val Ser Pro Asp Asp Val Val Gly Ile Leu Gly Gln Lys Arg
 315                 320                 325
```

```
ttc tgg aga gca agg aaa gcc att gcc aat caa caa aga gta ttt gct    1362
Phe Trp Arg Ala Arg Lys Ala Ile Ala Asn Gln Gln Arg Val Phe Ala
330             335                 340                 345 gtt caa cta ttt gag ttg cac aga ctg att aag gtt caa aaa ctt att    1410
Val Gln Leu Phe Glu Leu His Arg Leu Ile Lys Val Gln Lys Leu Ile
        350                 355                 360 gct gca tca ccg gat ctc ttg ctc gat gag atc agt ttt ctt gga aaa    1458
Ala Ala Ser Pro Asp Leu Leu Leu Asp Glu Ile Ser Phe Leu Gly Lys
            365                 370                 375 gtt tct gct aaa agc tat cca gtg aag aag ctc ctt cca tca gaa ttt    1506
Val Ser Ala Lys Ser Tyr Pro Val Lys Lys Leu Leu Pro Ser Glu Phe
                380                 385                 390 ctg gta aag cct cct cta cca cat gtt gtc gtc aaa caa agg ggt gac    1554
Leu Val Lys Pro Pro Leu Pro His Val Val Val Lys Gln Arg Gly Asp
    395                 400                 405 tcg gag aag act gac caa cat aaa atg gaa agc tca gct gag aac gta    1602
Ser Glu Lys Thr Asp Gln His Lys Met Glu Ser Ser Ala Glu Asn Val
410                 415                 420                 425 gtt ggg agg ttg tca aat caa ggt cat cat caa cat cca act aca tgc    1650
Val Gly Arg Leu Ser Asn Gln Gly His His Gln His Pro Thr Thr Cys
                430                 435                 440 ctt ttc cag caa aca acc cac cgg ctt cac cgg ctc caa atg gat att    1698
Leu Phe Gln Gln Thr Thr His Arg Leu His Arg Leu Gln Met Asp Ile
        445                 450                 455 gct ttc ctc ctc agc ctc ctc ttc cag gaa atc atc agc aat ggt gat    1746
Ala Phe Leu Leu Ser Leu Leu Leu Gln Glu Ile Ile Ser Asn Gly Asp
            460                 465                 470 ccc tgt aat gtc tcc ctc gga agg act gat ata cag cct cac cca ggt    1794
Pro Cys Asn Val Ser Leu Gly Arg Thr Asp Ile Gln Pro His Pro Gly
    475                 480                 485 atg gca cac acg ggg cat tat gga gga tat tat ggt cat tat atg cct    1842
Met Ala His Thr Gly His Tyr Gly Gly Tyr Tyr Gly His Tyr Met Pro
490                 495                 500                 505 aca cca atg gta atg cct caa tat cac ccc ggc atg gga ttc cca cct    1890
Thr Pro Met Val Met Pro Gln Tyr His Pro Gly Met Gly Phe Pro Pro
                510                 515                 520 cct ggt aat ggc tac ttc cct cca tat gga atg atg ccc acc ata atg    1938
Pro Gly Asn Gly Tyr Phe Pro Pro Tyr Gly Met Met Pro Thr Ile Met
        525                 530                 535 aac cca tat tgt tca agc caa caa caa caa caa caa ccc aat gag       1986
Asn Pro Tyr Cys Ser Ser Gln Gln Gln Gln Gln Gln Pro Asn Glu
            540                 545                 550 caa atg aac cag ttt gga cat cct gga aat ctt cag aac acc caa caa    2034
Gln Met Asn Gln Phe Gly His Pro Gly Asn Leu Gln Asn Thr Gln Gln
    555                 560                 565 caa caa cag aga tct gat aat gaa cct gct cca cag caa cag caa cag    2082
Gln Gln Gln Arg Ser Asp Asn Glu Pro Ala Pro Gln Gln Gln Gln Gln
570                 575                 580                 585 cca aca aag tct tat ccg cga gca aga aag agc agg caa ggg agc aca    2130
Pro Thr Lys Ser Tyr Pro Arg Ala Arg Lys Ser Arg Gln Gly Ser Thr
                590                 595                 600 gga agc agt cca agt ggg cca cag gga atc tct ggt agc aag tcc ttt    2178
Gly Ser Ser Pro Ser Gly Pro Gln Gly Ile Ser Gly Ser Lys Ser Phe
        605                 610                 615 ggg cca ttc gca gcc gtt gat gag gac agc aac atc aac aat gca cct    2226
Gly Pro Phe Ala Ala Val Asp Glu Asp Ser Asn Ile Asn Asn Ala Pro
    620                 625                 630 gag caa acg atg aca aca acc aca acg aca aga aca act gtt act       2274
Glu Gln Thr Met Thr Thr Thr Thr Thr Thr Arg Thr Thr Val Thr
635                 640                 645
```

-continued

```
cag aca aca aga gat ggg gga gga gtg acg aga gtg ata aag gtg gta    2322
Gln Thr Thr Arg Asp Gly Gly Gly Val Thr Arg Val Ile Lys Val Val
650                 655                 660                 665 cct cac aac gca aag ctc gcg agt gag aat gct gcc aga att ttc cag    2370
Pro His Asn Ala Lys Leu Ala Ser Glu Asn Ala Ala Arg Ile Phe Gln
                670                 675                 680 tca ata caa gaa gaa cgt aaa cgc tat gac tcc tct aag cct            2412
Ser Ile Gln Glu Glu Arg Lys Arg Tyr Asp Ser Ser Lys Pro
            685                 690                 695 taatcctctc tatgcgtatt gtacttgata tgtattttac aaaattagaa aaattgtgat  2472
agatgttatc ctcaatatat gtaccatgta aacgtattat ggtgtaagcc tcatttatat  2532
gtgttaattt gtcttaaagc cttgaaatca aaaaaaaaaa aaaaaaaaaa aaaaaaaaaa  2592
aaaaaaaaaa aaaa                                                    2606

<210> SEQ ID NO 4
<211> LENGTH: 595
<212> TYPE: PRT
<213> ORGANISM: Arabidopsis thaliana

<400> SEQUENCE: 4

Gln Met Ser Phe Met Glu Asn Val Arg Ser Ala Gln His Asp Gln
1               5                   10                  15

Arg Lys Met Val Arg Glu Glu Asp Phe Ala Val Pro Val Tyr Ile
                20                  25                  30

Asn Ser Arg Arg Ser Gln Ser His Gly Arg Thr Lys Ser Gly Ile Glu
            35                  40                  45

Lys Glu Lys His Thr Pro Met Val Ala Pro Ser His His Ser Ile
50                  55                  60

Arg Phe Gln Glu Val Asn Gln Thr Gly Ser Lys Gln Asn Val Cys Leu
65                  70                  75                  80

Ala Thr Cys Ser Lys Pro Glu Val Arg Asp Gln Val Lys Ala Asn Arg
                85                  90                  95

Arg Ser Gly Gly Phe Val Ile Ser Leu Asp Val Ser Val Thr Glu Glu
                100                 105                 110

Ile Asp Leu Glu Lys Ser Ala Ser Ser His Asp Arg Val Asn Asp Tyr
            115                 120                 125

Asn Ala Ser Leu Arg Gln Glu Ser Arg Asn Arg Leu Tyr Arg Asp Gly
130                 135                 140

Gly Lys Thr Arg Leu Lys Asp Thr Asp Asn Gly Ala Glu Ser His Leu
145                 150                 155                 160

Ala Thr Glu Asn His Ser Gln Glu Gly His Gly Ser Pro Glu Asp Ile
                165                 170                 175

Asp Asn Asp Arg Glu Tyr Ser Lys Ser Arg Ala Cys Ala Ser Leu Gln
            180                 185                 190

Gln Ile Asn Glu Glu Ala Ser Asp Asp Val Ser Asp Ser Met Val
            195                 200                 205

Asp Ser Ile Ser Ser Ile Asp Val Ser Pro Asp Val Val Gly Ile
        210                 215                 220

Leu Gly Gln Lys Arg Phe Trp Arg Ala Arg Lys Ala Ile Ala Asn Gln
225                 230                 235                 240

Gln Arg Val Phe Ala Val Gln Leu Phe Glu Leu His Arg Leu Ile Lys
                245                 250                 255

Val Gln Lys Leu Ile Ala Ala Ser Pro Asp Leu Leu Leu Asp Glu Ile
                260                 265                 270
```

-continued

```
Ser Phe Leu Gly Lys Val Ser Ala Lys Ser Tyr Pro Val Lys Lys Leu
        275                 280                 285

Leu Pro Ser Glu Phe Leu Val Lys Pro Pro Leu Pro His Val Val Val
    290                 295                 300

Lys Gln Arg Gly Asp Ser Glu Lys Thr Asp Gln His Lys Met Glu Ser
305                 310                 315                 320

Ser Ala Glu Asn Val Val Gly Arg Leu Ser Asn Gln Gly His His Gln
                325                 330                 335

His Pro Thr Thr Cys Leu Phe Gln Gln Thr Thr His Arg Leu His Arg
            340                 345                 350

Leu Gln Met Asp Ile Ala Phe Leu Leu Ser Leu Leu Leu Gln Glu Ile
        355                 360                 365

Ile Ser Asn Gly Asp Pro Cys Asn Val Ser Leu Gly Arg Thr Asp Ile
    370                 375                 380

Gln Pro His Pro Gly Met Ala His Thr Gly His Tyr Gly Gly Tyr Tyr
385                 390                 395                 400

Gly His Tyr Met Pro Thr Pro Met Val Met Pro Gln Tyr His Pro Gly
                405                 410                 415

Met Gly Phe Pro Pro Gly Asn Gly Tyr Phe Pro Pro Tyr Gly Met
            420                 425                 430

Met Pro Thr Ile Met Asn Pro Tyr Cys Ser Ser Gln Gln Gln Gln Gln
        435                 440                 445

Gln Gln Pro Asn Glu Gln Met Asn Gln Phe Gly His Pro Gly Asn Leu
    450                 455                 460

Gln Asn Thr Gln Gln Gln Gln Arg Ser Asp Asn Glu Pro Ala Pro
465                 470                 475                 480

Gln Gln Gln Gln Gln Pro Thr Lys Ser Tyr Pro Arg Ala Arg Lys Ser
                485                 490                 495

Arg Gln Gly Ser Thr Gly Ser Ser Pro Ser Gly Pro Gln Gly Ile Ser
            500                 505                 510

Gly Ser Lys Ser Phe Gly Pro Phe Ala Ala Val Asp Glu Asp Ser Asn
        515                 520                 525

Ile Asn Asn Ala Pro Glu Gln Thr Met Thr Thr Thr Thr Thr Thr Thr
    530                 535                 540

Arg Thr Thr Val Thr Gln Thr Thr Arg Asp Gly Gly Val Thr Arg
545                 550                 555                 560

Val Ile Lys Val Val Pro His Asn Ala Lys Leu Ala Ser Glu Asn Ala
                565                 570                 575

Ala Arg Ile Phe Gln Ser Ile Gln Glu Glu Arg Lys Arg Tyr Asp Ser
            580                 585                 590

Ser Lys Pro
        595

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 5
ctttcccacc aacgctgatc                                                 20

<210> SEQ ID NO 6
<211> LENGTH: 23
```

```
<212> TYPE: DNA
<213> ORGANISM: Artificial Sequence
<220> FEATURE:
<223> OTHER INFORMATION: Description of Artificial Sequence:primer

<400> SEQUENCE: 6
gtacagcgaa gaggcagtca acg                                           23

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 7
tacgctcgag atcacgaaaa tgtatat                                       27

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 8
agtacccggg ctttggatcg acaaa                                         25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 9
gttatctaga tggatcgtag ttgca                                         25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 10 aattctcga gcgccaaact tttagtga                                       27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 11
gttactcgag gtatcacgaa aatgt                                         25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 12
```

```
ctctcccggg cactcacaat tcaca                                                25
```

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 13

```
taagctcgag cgtagttgca tttta                                                25
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 14

```
ctctcccggg cactcacaat tcaca                                                25
```

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 15

```
cattctcgag gttggaccgg ctctgtg                                              27
```

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 16

```
ctctcccggg cactcacaat tcaca                                                25
```

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 17

```
gtggctcgag tttattgaag cttatcg                                              27
```

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 18

```
ctctcccggg cactcacaat tcaca                                                25
```

<210> SEQ ID NO 19
<211> LENGTH: 25
<212> TYPE: DNA
<213> ORGANISM: Artificial Sequence

```
<220> FEATURE:
<223> OTHER INFORMATION: Description of Artificial Sequence:primer

<400> SEQUENCE: 19
gttactcgag gtatcacgaa aatgt                                    25

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 20
acgacccggg tcaataaaac aaacccac                                 28

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 21
gttactcgag gtatcacgaa aatgt                                    25

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 22
acaccccggg ggtccaacgt ttttaatg                                 28

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 23
taagctcgag cgtagttgca tttta                                    25

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 24
acgacccggg tcaataaaac aaacccac                                 28

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 25
taagctcgag cgtagttgca tttta                                    25
```

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 26
acaccccggg ggtccaacgt ttttaatg                                28

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 27
taagctcgag cgtagttgca tttta                                  25

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 28
gtttcccggg tactaatcga gaaaca                                 26

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 29
gaattctcga gaagacatga gacaat                                 26

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 30
ctctcccggg cactcacaat tcaca                                  25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 31
tttcccgggt taagacaaat taac                                   24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:primer

```
<400> SEQUENCE: 32
tagtatcgat acaagcactt tggt                                              24
```

What is claiimed is:

1. An isolated regulatory DNA sequence comprising the nucleotide sequence of SEQ ID NO: 1 or a portion of said nucleotide sequence that promotes root knot and cyst nematode inducible transcription of a heterologous DNA operably linked thereto.

2. The regulatory DNA sequence according to claim 1, wherein said regulatory DNA sequence is nematode feeding site-specific.

3. A chimeric DNA sequence comprising in the direction of transcription:
   (i) the regulatory DNA sequence according to claim 1; and
   (ii) a DNA sequence to be expressed under the transcriptional control of said regulatory DNA sequence, wherein said DNA sequence to be expressed is not naturally under the transcriptional control of said regulatory DNA sequence.

4. The chimeric DNA sequence according to claim 3, wherein said DNA sequence to be expressed encodes of a plant cell-disruptive substance.

5. The chimeric DNA sequence according to claim 4, wherein said plant cell-disruptive substance is barnase.

6. The chimeric DNA sequence according to claim 3, wherein said DNA sequence to be expressed encodes of a nematode feeding site-disruptive substance.

7. The chimeric DNA sequence according to claim 6, wherein said nematode feeding site-disruptive substance comprises RNA complementary to RNA essential to cell viability.

8. A replicon comprising the chiMeric DNA sequence according to claim 3.

9. A replicon comprising in the direction of transcription:
   (i) the regulatory DNA sequence wherein said recognition site is downstream and operably linked to said regulatory DNA sequence according to claim 1, and
   (ii) at least one recognition site for a restriction endonuclease for insertion of a DNA sequence to be expressed under the control of said regulatory DNA sequence.

10. A micro organism containing the replicon according to claim 8.

11. A plant cell having stably incorporated into its genome the chimeric DNA sequence according to claim 3.

12. A root system of a plant consisting essentially of cells according to claim 11.

13. A plant consisting essentially of cells according to claim 11.

14. The plant according to claim 13, which plant is a dicotyledonous plant.

15. The plant according to claim 14, which plant is a potato plant.

16. A plant grafted onto the root system according to claim 12, wherein said plant includes the root system according to claim 12 and a plant portion grafted onto said root system.

17. A part of a plant that is selected from the group consisting of seeds, flowers, tubers, roots, leaves, fruts, pollen and wood, wherein said part is obtained from the plant according to claim 13 and includes said plant cells.

18. A crop consisting essentially of the plant according to claim 13.

19. A method of producing a transgenic plant comprising transforming a plant with the chimeric DNA sequence according to claim 3, thereby producing a transgenic plant.

* * * * *